(12) United States Patent
Grabek et al.

(10) Patent No.: US 6,231,518 B1
(45) Date of Patent: May 15, 2001

(54) INTRAPERICARDIAL ELECTROPHYSIOLOGICAL PROCEDURES

(75) Inventors: James R. Grabek, Long Lake; Carl M. Beaurline, Mendota Heights; Cecil C. Schmidt, Edina; Lawrence A. Lundeen, Blaine; Patricia J. Rieger, Prior Lake, all of MN (US)

(73) Assignee: Comedicus Incorporated, Columbia Heights, MN (US)

( * ) Notice: Subject to any disclaimer, the term of this patent is extended or adjusted under 35 U.S.C. 154(b) by 0 days.

(21) Appl. No.: 09/084,461

(22) Filed: May 26, 1998

(51) Int. Cl.$^7$ ........................................................ A61B 5/04

(52) U.S. Cl. ............................................................. 600/508

(58) Field of Search .................................... 600/374, 508, 600/509; 606/129; 607/115, 116, 129, 130

(56) References Cited

U.S. PATENT DOCUMENTS

| | | |
|---|---|---|
| 3,923,060 | 12/1975 | Ellinwood, Jr. . |
| 4,003,379 | 1/1977 | Ellinwood, Jr. . |
| 4,027,510 | 6/1977 | Hiltebrandt . |
| 4,620,547 | 11/1986 | Boebel . |
| 4,651,753 | 3/1987 | Lifton . |
| 4,656,999 | 4/1987 | Storz . |
| 4,690,148 * | 9/1987 | Hess ..................................... 600/374 |
| 4,759,348 | 7/1988 | Cawood . |
| 4,991,578 | 2/1991 | Cohen et al. . |
| 5,033,477 | 7/1991 | Chin et al. . |
| 5,046,504 | 9/1991 | Albert et al. . |
| 5,071,412 | 12/1991 | Noda . |
| 5,071,428 | 12/1991 | Chin et al. . |
| 5,087,243 | 2/1992 | Avitall . |
| 5,127,421 * | 7/1992 | Bush et al. ........................... 607/130 |
| 5,213,570 | 5/1993 | VanDeripe . |
| 5,220,917 | 6/1993 | Cammilli et al. . |
| 5,235,966 | 8/1993 | Jamner . |
| 5,249,574 | 10/1993 | Bush et al. . |
| 5,269,326 | 12/1993 | Verrier . |
| 5,281,230 | 1/1994 | Heidmueller . |
| 5,290,299 | 3/1994 | Fain et al. . |
| 5,318,589 | 6/1994 | Lichtman . |
| 5,336,252 | 8/1994 | Cohen . |
| 5,385,156 | 1/1995 | Oliva . |
| 5,387,419 | 2/1995 | Levy et al. . |
| 5,395,312 | 3/1995 | Desai . |

(List continued on next page.)

FOREIGN PATENT DOCUMENTS

| | | |
|---|---|---|
| 0 417 031 A2 | 3/1991 | (EP) . |
| 0 706 781 A2 | 4/1996 | (EP) . |
| 0 888 750 A1 | 1/1999 | (EP) . |
| WO 95/17919 | 7/1995 | (WO) . |
| WO 96/22056 | 7/1996 | (WO) . |
| WO 96/40368 | 12/1996 | (WO) . |
| WO 97/16170 | 5/1997 | (WO) . |
| WO 98/05289 | 2/1998 | (WO) . |

OTHER PUBLICATIONS

Catalog pages of Portlyn Medical Products, pp. 4, 24 and 25 (1997).

Sosa et al., "A New Technique to Perform Epicardial Mapping in the Electrophysiology Laboratory," *Journal of Cardiovascular Electrophysiology*, 7(6):531–536 (Jun. 1996).

(List continued on next page.)

*Primary Examiner*—William E. Kamm
(74) *Attorney, Agent, or Firm*—Merchant & Gould P.C.

(57) ABSTRACT

Methods and devices for diagnosis and treatment of cardiac conditions through the pericardial space are disclosed which are particularly suited for performing minimally invasive procedures from the surface of the heart including electrophysiology mapping and ablation, drug delivery, restenosis prevention, stent placement, etc. Some embodiments of a device disclosed herein can also be used advantageously to perform a medical procedure in a selected lumen of a patient's body.

20 Claims, 20 Drawing Sheets

U.S. PATENT DOCUMENTS

| | | |
|---|---|---|
| 5,452,733 | 9/1995 | Sterman et al. . |
| 5,496,310 | 3/1996 | Exconde et al. . |
| 5,536,251 | 7/1996 | Evard et al. . |
| 5,634,895 | 6/1997 | Igo et al. . |
| 5,681,278 | 10/1997 | Igo et al. . |
| 5,702,716 | 12/1997 | Dunn et al. . |
| 5,735,290 | 4/1998 | Sterman et al. . |
| 5,797,870 | 8/1998 | March et al. . |

OTHER PUBLICATIONS

Brochure, Portlyn Medical Products: A total manufacturing capability dedicated to medical products and components (1993).

Product Description Sheet by Comedicus Incorporated for "A New Approach: Access The Pericardial Space With The PerDUCER™ Pericardial Access Device".

Medical Device & Diagnostic Industry, Advertisement, "Spectrum . . . precision from start to finish".

Advertisement "Corrosion–Resistant Alloys," Ulbrich Stainless Steels & Special Metals Inc.

Surgical Instruments, Advertisement for T.A.G. Medical Products Ltd.

Medical Date International, Inc., "Arrhythmia Management Market: Emerging Trends, Technologies and Business Opportunities," pp. ES–1–43 (1993).

Dain Bosworth, Cardima, Inc., "Equity Research Report" (1997).

Brochure, "Cardiac Pathways, Arrhythmia Mapping System," Cardiac Pathways Corporation.

Brochure, Elecath, "Genesis Diagnostic Steerables".

The Biosense Bulletin, 1(1):6 pages (Mar. 1997).

Ben–Haim et al., "Nonfluoroscopic, in vitro navigation and mapping technology," *Nature Medicine*, 2(12):1393–1394 (Dec. 1996).

Brochure, EP—WORKMATE™, "The Only Computerized EP Recording System with an Integrated Stimulator," EP MedSystems Looking Forward to the Future (Apr. 1997).

Brochure, "Living Anatomy" Live Lecture Series, Biosense.

Krikorian et al., "Pericardiocentesis," *The American Journal of Medicine*, 65:808–814 (Nov. 1978).

Editorial, "Intravascular radiation for restenosis prevention: could it be the holy grail?", *Heart*, 76:99–100(1996).

The PerDUCER®, Pericardial Access Device Training Manual, Jan. 1998 Piper Jaffray, Novoste, 24 pages, Sep. 1996.

Hirau et al., "Electrophysiology of the Atrio—AV Nodal Inputs and Exists in the Normal Dog Heart: Radiofrequency Ablation Using an Epicardial Approach," *J. of Cardiovascular Electrophysiology*, 8(8):904–915 (Aug. 1997).

* cited by examiner

INTRAPERICARDIAL ELECTROPHYSIOLOGICAL PROCEDURES

FIELD OF THE INVENTION

The present invention is directed to minimally invasive medical procedures. More specifically, the disclosure provides apparatuses and methods for treating and diagnosing cardiac conditions from the intrapericardial space. The disclosure also provides new and advantageous pericardial access devices and kits.

BACKGROUND OF THE INVENTION

Knowledge of the pericardium (pericardial sac) dates back to the time of Galen (129–200 A.D.) the Greek physician and anatomist who created the term "pericardium." The pericardium (pericardial sac) is a conical membranous sac in which the heart and the commencement of the great vessels are contained. *Gray's Anatomy* (1977 ed.) pp. 457–460. The pericardium is fluid-filled and functions to prevent dilation of the chambers of the heart, lubricates the surfaces of the heart, and maintains the heart in a fixed geometric position. It also provides a barrier to the spread of infection from adjacent structures in the chest cavity and prevents surrounding tissue(s) from adhering to the heart. The space between the pericardium and the heart, known as the pericardial space, is normally small in volume and includes fluid therein. It has been reported that when fluid is injected into the pericardial space it accumulates in the atrioventricular and interventricular grooves, but not over the ventricular surfaces. See, Shabetai R, "Pericardial and Cardiac Pressure," in *Circulation*, 77:1 (1988).

Pericardiocentesis, or puncture of the pericardium has been performed for: 1) diagnosis of pericardial disease(s) by study of the pericardial fluid; 2) withdrawal of pericardial fluid for the treatment of acute cardiac tamponade; and 3) infusion of therapeutic agents.

Methods for accessing the pericardial space are known. For example, U.S. Pat. No. 5,071,428 (Chin et al.) discloses a method and apparatus for accessing the pericardial space for the insertion of implantable defibrillation leads. This method requires gripping the pericardium with a forceps device and cutting the pericardium with a scalpel (pericardiotomy) under direct vision through a subxiphoid surgical incision.

Uchida Y., et al., "Angiogenic Therapy of acute Myocardial Infarction by Intrapericardial Injection of Basic Fibroblast Growth Factor and Heparin Sulfate," in *Circulation AHA Abstracts* (1994), reported a method for the intrapericardial injection of angiogenic agents. While not described in detail, this method generally involved the percutaneous transcatheter bolus injection of drugs into the pericardial cavity via the right atrium.

U.S. Pat. No. 4,991,578 also discloses apparatuses and methods for accessing the pericardial space for placement of defibrillation electrodes. One apparatus disclosed uses suction to "pull" the pericardium against a perforating needle housed in an outer catheter, thus impaling the pericardium on the needle. Another apparatus disclosed includes a catheter through which suction is applied to draw the pericardium into the lumen of the catheter. Once drawn in, a wire suture is applied to stabilize the pericardium to the catheter, a piercing needle inserted through the pericardium, and a guidewire passed through the needle into the pericardial space. This patent also discloses accessing the pericardium from the outside (i.e., through the parietal pericardial layer) with a needle after separating the outer layer from the epicardial layer by distending the pericardial space with a fluid passed into the space through a perforation made through the atrial wall.

U.S. Pat. No. 5,269,326 discloses passing a catheter into the right atrium and puncturing through the right auricle tangential to and between the epicardium and pericardium. U.S. Pat. No. 5,336,252 discloses a tri-lumen apparatus for accessing the pericardial space to implant electrical leads in the pericardial space.

The present invention provides new devices for accessing the pericardial space as well as kits and methods for performing diagnostic and medical procedures in the pericardial space.

SUMMARY OF THE INVENTION

The present invention is directed to methods and devices for diagnosis and treatment of cardiac conditions through the pericardial space. Preferred embodiments of pericardial access devices for accessing the pericardial space to perform procedures according to the invention are described.

It will be noted that in several places throughout the specification, guidance is provided through lists of examples. In each instance, the recited list serves only as a representative group. It is not meant, however, that the list is exclusive.

Preferred pericardial access devices according to the invention use suction or mechanical grasping during access of the pericardium. The preferred devices provide for separating the parietal pericardium from the epicardial surface of the heart to reduce the chance of trauma to the heart wall during access of the pericardial space. Once the pericardial space is accessed, a material transport tube can be placed into the pericardial space for administering or removing materials from the pericardial space.

Procedures which can be performed from the pericardial space according to the invention include, for example, collection of pericardial fluid, pericardial biopsy, diagnostic and therapeutic agent delivery, placement of electrical leads, electrophysiology mapping and ablation, angioplasty, restenosis reduction, coronary vessel stent placement, coronary vessel bypass grafting, etc.

The invention also provides kits including components necessary for performing a selected procedure through the pericardial space.

The pericardial access devices of the invention can also be used for performing various medical procedures in a selected lumen of the patient's body.

DETAILED DESCRIPTION OF THE INVENTION

Figure 1:
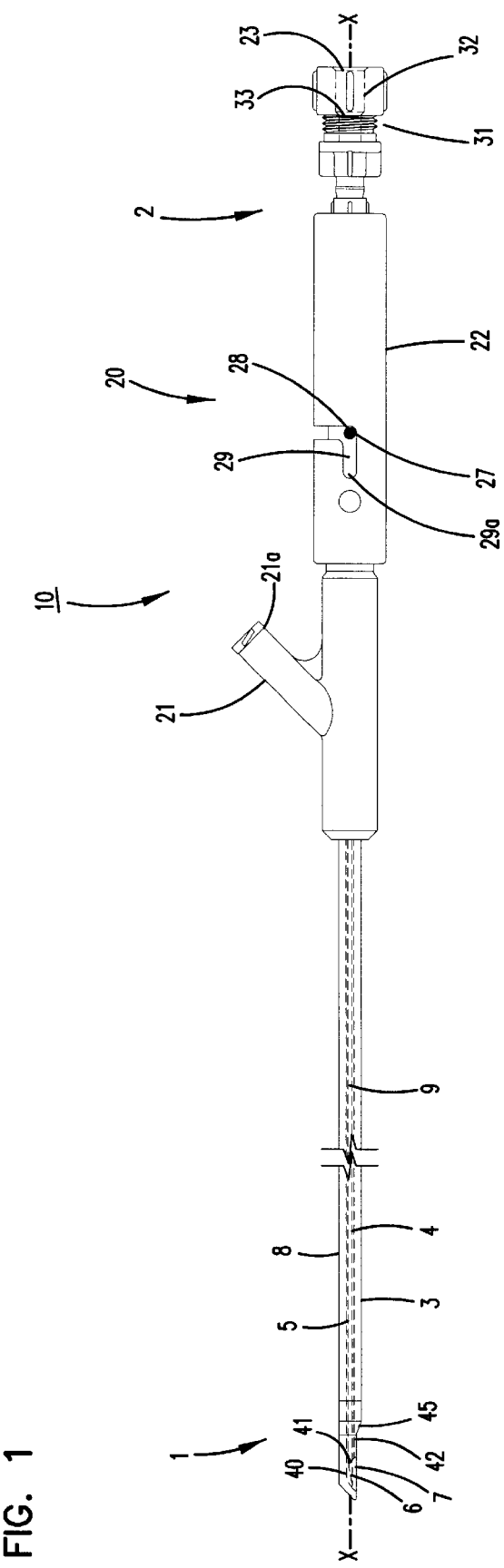
FIG. 1 is a side view of one embodiment of a pericardial access device according to the invention.

The present invention provides systems and procedures for accessing the pericardial space and diagnosing and treating conditions of the heart through the pericardial space. The devices and methods disclosed can be used for a human or non-human patient. The procedures disclosed are particularly suited for use with minimally invasive techniques, however, it will be appreciated that the devices and methods can also be used with open chest thoracotomy procedures.

Minimally invasive systems for accessing the pericardial space with reduced chance of injury to the heart are relatively new. Unlike prior systems which access the pericardial space by passing a needle from the endocardial surface of the heart through the visceral pericardium into the pericardial space (i.e., "inside-out"), preferred methods of the present invention provide access to the pericardial space through the parietal pericardium (i.e., "outside-in"). Access to the pericardial space from the outside-in can be visualized using known visualization systems for monitoring other minimally invasive procedures, such as endoscopy, fluoroscopy, ultrasonograpy, etc.

I. Pericardial Access Device

Methods for accessing the pericardial space from the inside-out are disclosed in, for example, U.S. Pat. Nos. 4,991,578 and 5,269,326. The disclosure of both of these patents are incorporated herein by reference. However, unlike inside-out procedures, the preferred methods of the present invention reduce the chance of injury to the heart and do not require puncturing the heart wall to gain access to the pericardial space.

A. Suction Devices

One pericardial access device for performing an outside-in approach to the pericardial space is the PerDUCER®. This device is presently in clinical trials and will be available from Comedicus Incorporated, 3839 Central Avenue N.E., Columbia Heights, Minn. 55431, the assignee of the present invention. The PerDUCER® uses suction to lift a portion of the pericardium away from the heart to provide a suitable location for penetration of the pericardium with low risk of injury to the epicardial surface of the heart. The portion of pericardium lifted away from the heart can be referred to as a "bleb." Once formed, the bleb can be punctured by a piercing instrument, such as a hollow needle, that travels into the bleb in a direction tangential to the epicardial surface of the heart.

Co-pending U.S. patent applications Ser. Nos. 08/933,858 and 08/934,045, now U.S. Pat. No. 5,972,013, disclose new and advantageous devices for outside-in access to the pericardial space through penetration of a suction formed bleb in a direction substantially perpendicular to the heart. U.S. Ser. No. 08/933,858 discloses a unique outer guide tube constructed with an inner "shoulder" to stabilize the bleb of pericardium during penetration of the pericardium. U.S. Ser. No. 08/934,045, now U.S. Pat. No. 5,972,013, discloses an outer guide tube constructed to deflect the penetrating body to enter the bleb of pericardium at a selected angle during penetration of the pericardium. The entire disclosure of both of these applications are incorporated herein by reference.

Some pericardial access devices do not use suction to lift the pericardium away from the epicardial surface of the heart. For example, co-pending application U.S. Se. No. 08/761,189, now U.S. Pat. No. 5,931,810, mechanically grasps the parietal pericardium between grasping surfaces for lifting a portion of the pericardium a sufficient distance from the epicardial surface before entering the pericardial space with a penetrating body that passes into the pericardial space between the grasping surfaces. The entire disclosure of this application is also incorporated herein by reference. An improved mechanical grasping device for pericardial access is described below.

The following is a detailed description of a pericardial access device providing advantageous features for greater precision of needle penetration into the pericardium and placement of a guidewire into the pericardial space. Throughout the various drawing figures, identical elements are numbered identically.

Figure 2:
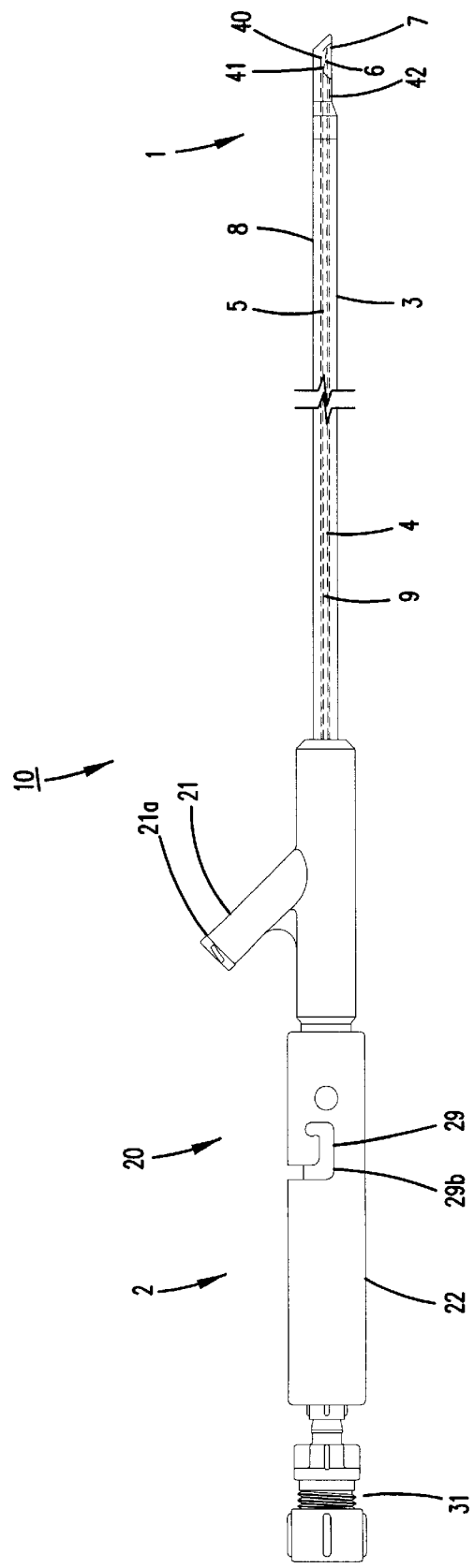
FIG. 2 is an opposite side view of the pericardial access device of FIG. 1.
Figure 3:
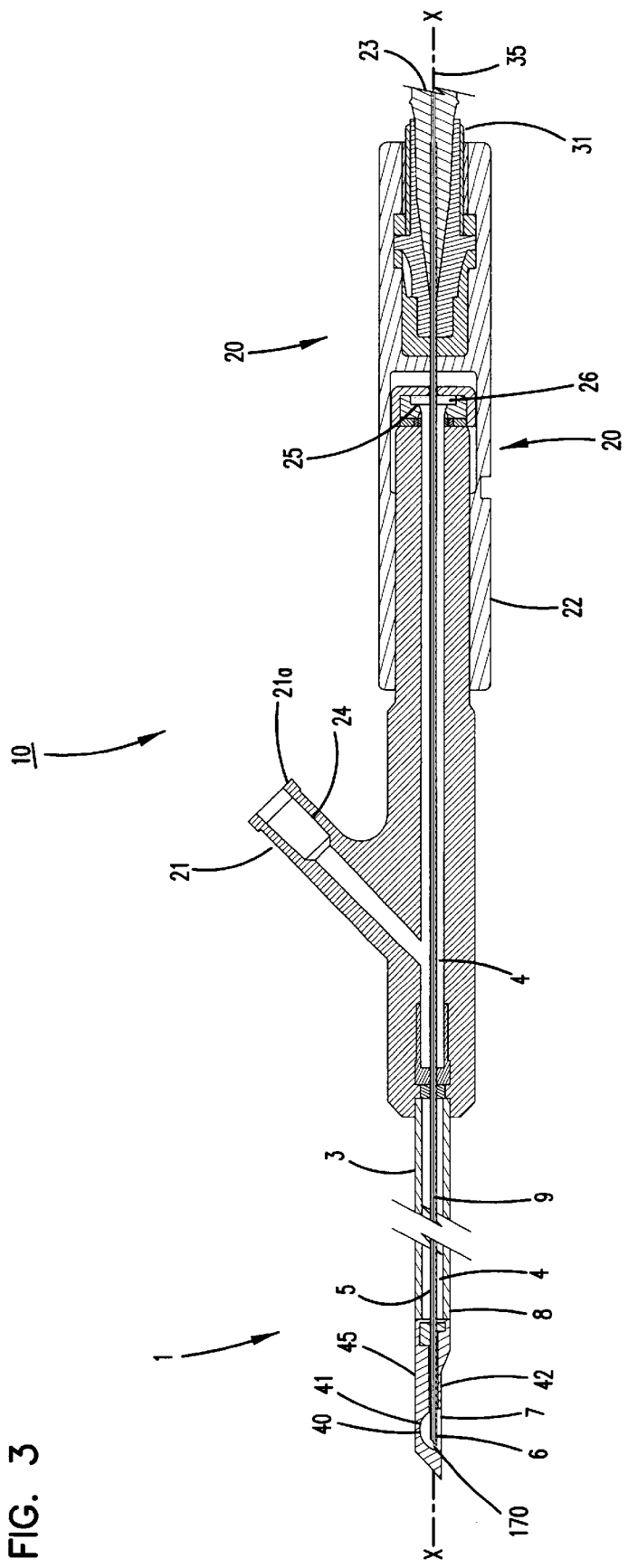
FIG. 3 is a longitudinal cross section view of the pericardial access device of FIGS. 1 and 2.
Figure 4:
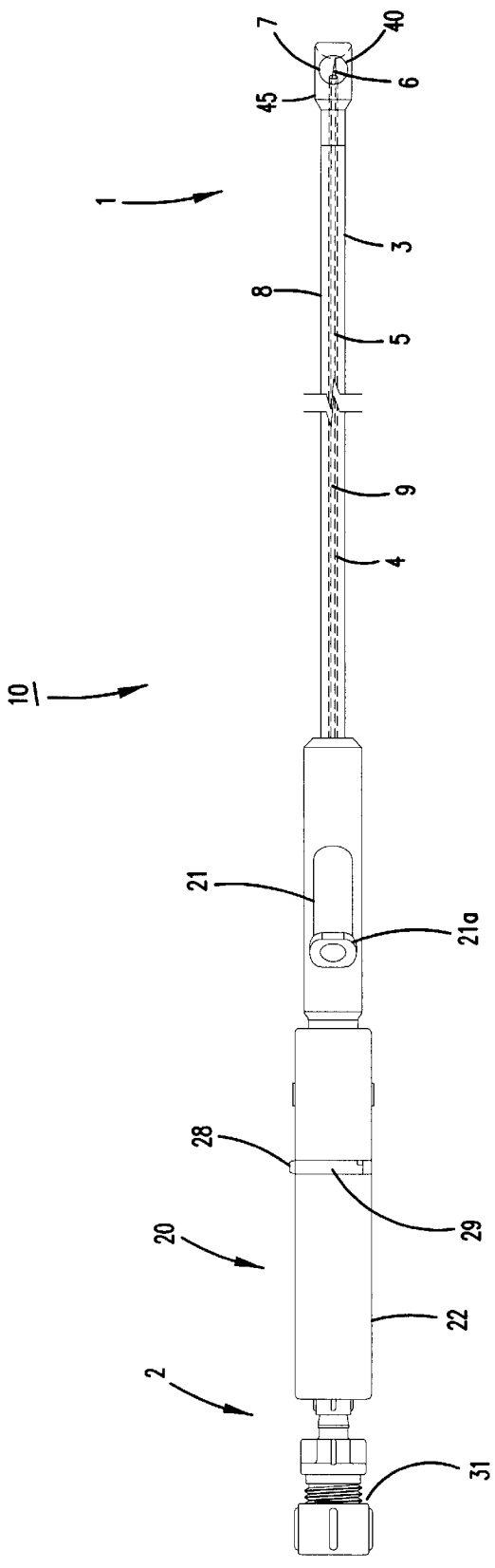
FIG. 4 is a top view of the pericardial access device of FIGS. 1–3.

Referring to FIGS. 1–4, FIG. 1 is a first side view of a pericardial access device 10; FIG. 2 is an opposite side view of the pericardial access device 10; FIG. 3 is a longitudinal cross-section view of the pericardial access device 10; and FIG. 4 is a top view of pericardial access device 10. As illustrated, the pericardial access device 10 has a distal end 1 and a proximal end 2. The device 10 includes an elongate tubular body 3 having a lumen 4 that is of a size sufficient to permit axial movement of a penetrating body 5 which has a lumen 9 and a piercing distal end 6. At distal end 1, the pericardial access device 10 includes a distal opening 7 in the sidewall 8 of elongate tubular body 3.

At the proximal end 2, the pericardial access device 10 includes a handle arrangement 20 for manipulation and operation of the device. In the illustrated embodiment, the handle arrangement 20 includes a vacuum inlet 21, operating sleeve 22 and a guidewire port 23. The vacuum inlet 21 includes a vacuum channel 24 that is in fluid communication with lumen 4 of the elongate tubular body 3. The proximal end of the vacuum inlet 21 includes a connector 21 a such as a Luer fitting or threads, for connecting the vacuum source (not shown) to the device 10. The device 10 also includes a sealing mechanism 25 such as a gasket 26 at a point proximal to the vacuum inlet channel 24 which, when a vacuum is applied to the lumen 4, permits axial movement of penetrating body 5 without loss of suction to the lumen 4.

The operating sleeve 22 can be rotated around longitudinal axis X—X and includes a stopping mechanism 27 for limiting axial travel of penetrating body 5. In the illustrated embodiment, stopping mechanism 27 includes a pin 28 that travels within track 29 of operating sleeve 22. FIG. 1 illustrates the track position 29a when the track position 29b on the opposite side is in the position illustrated in FIG. 2. FIG. 4 is a top view illustrating the track position 29c relative to pin 28 when the stopping mechanism 27 is in the position illustrated in FIGS. 1 and 2.

In the illustrated embodiment, the guidewire port 23 is in fluid communication with lumen 9 of penetrating body 5. A Touhy-Borst valve system 31 can be used to fix the guidewire 35 at a selected location within lumen 9.

At the distal end 1, the distal opening 7 of pericardial access device 10 can be a depression 40 into the side wall 8 that is in fluid communication with penetrating body lumen 9. A hemicircular depression 41 is illustrated. When a vacuum is applied to lumen 4 of elongate tubular body 3, a bleb of pericardium forms within depression 40 that can be pierced by the piercing distal end 6 of penetrating body 5. It will be appreciated that the sidewall 8 of elongate tubular body 3 has a flattened surface 42 at the location of depression 40. The flattened surface 42 provides rotational stability of device 10 during use of the device. In the illustrated embodiment, the relative relationship of the flattened surface 42 and the vacuum inlet 21 permit the operator to verify the rotational orientation of the tip within the patient based on the orientation of the vacuum inlet 21 outside the patient. In a preferred embodiment, the side wall 8 includes a clear view tube 45 at the distal end 1 which is configured and arranged with the flattened surface 42 and depression 40.

Referring to FIGS. 5–8, the operation of pericardial access device 10 will now be described. Initially, a subxiphoid incision, or other incision providing access to the thorax, is made into the thorax and an introducer is passed through the mediastinum to the surface of the heart. The pericardial access device can then be passed through the introducer to the heart.

Figure 5A:
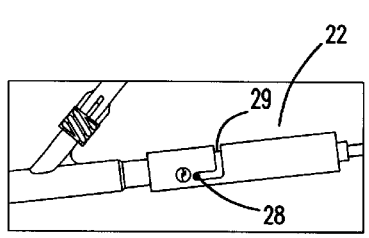
FIG. 5*a* illustrates the position of the operating sleeve of the pericardial access device of FIGS. 1–4 when the distal piercing end of the penetrating body is in the position illustrated in FIG. 5*b*.
Figure 5B:
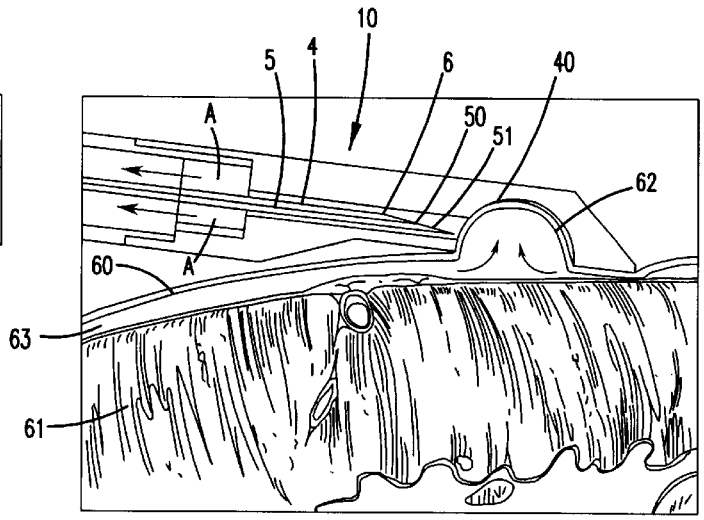
FIG. 5.

Referring to FIGS. 5a and 5b, the piercing distal end 6 of penetrating body 5 includes a beveled edge 50 and a distal opening 51 of lumen 9 (see FIG. 3) that passes through beveled edge 50. When pin 28 is oriented at the distal end of track 29, as illustrated, beveled edge 50 is oriented up. That is, the beveled edge 50 is rotated away from the surface of the heart 61. Application of suction (arrows A) through lumen 4 lifts a portion of pericardium 60 away from the heart 61 to form a "bleb" 62 in depression 40.

Figure 6A:
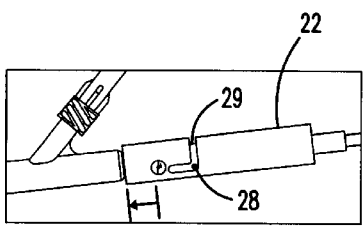
FIG. 6*a* illustrates the position of the operating sleeve of the pericardial access device of FIGS. 1–4 when the distal piercing end of the penetrating body is in the position illustrated in FIG. 6*b*.
Figure 6B:
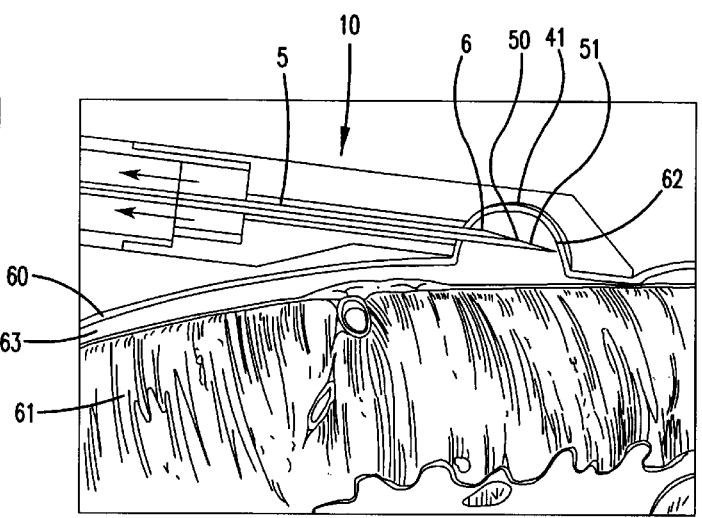
FIG. 6.

Referring now to FIGS. 6a and 6b, once bleb 62 is formed, the piercing distal end 6 of penetrating body 5 is advanced distally to penetrate the pericardium 61 and enter the pericardial space 63. As shown in FIG. 6a, when penetrating body 5 is distally advanced, pin 28 is at the proximal end of track 29.

Figure 7A:
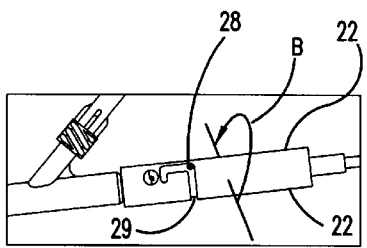
FIG. 7a illustrates the position of the operating sleeve of the pericardial access device of FIGS. 1–4 when the distal piercing end of the penetrating body is in the position illustrated in FIG. 7b.
Figure 7B:
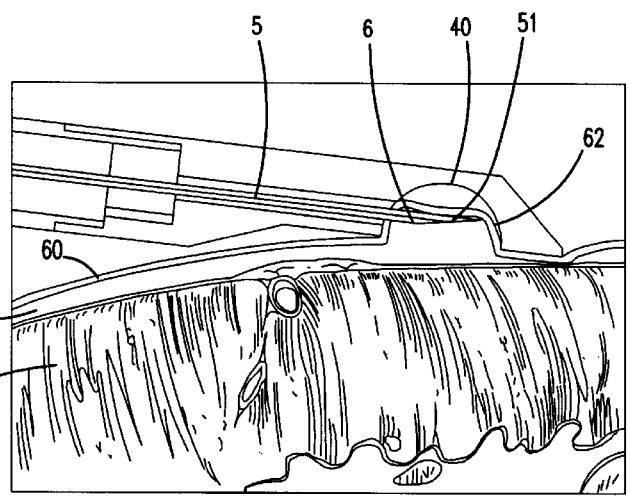
FIG. 7.

Referring now to FIGS. 7a and 6a, after penetration of bleb 62, operating sleeve 22 is rotated 180° (arrow B) so that bevel 51 is oriented towards the heart 61. Rotating bevel 51 (arrow B) facilitates passage of guidewire 35 into pericardial space 63. In this position, pin 28 is located within track 29 as illustrated in FIG. 6a.

Figure 8A:
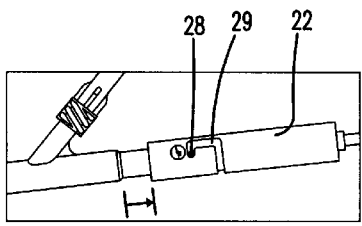
FIG. 8a illustrates the position of the operating sleeve of the pericardial access device of FIGS. 1–4 when the distal piercing end of the penetrating body is in the position illustrated in FIG. 8b.
Figure 8B:
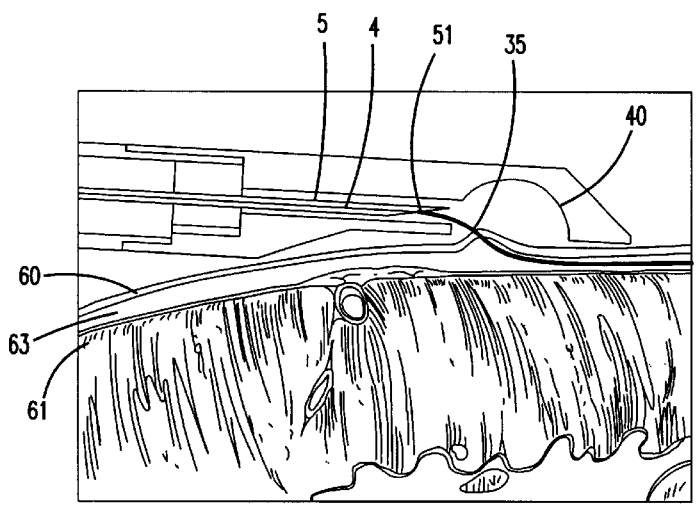
FIG. 8.

Referring to FIGS. 8a and 8b, after guidewire 35 has been passed into pericardial space 63, operating sleeve 22 is moved proximally to retract piercing distal end 6 proximally into lumen 4. In this position, pin 28 is positioned relative to track 29 as illustrated in FIG. 8a. Once guidewire 35 is in place in the pericardial space, pericardial access device 10 can be removed.

Figure 9:
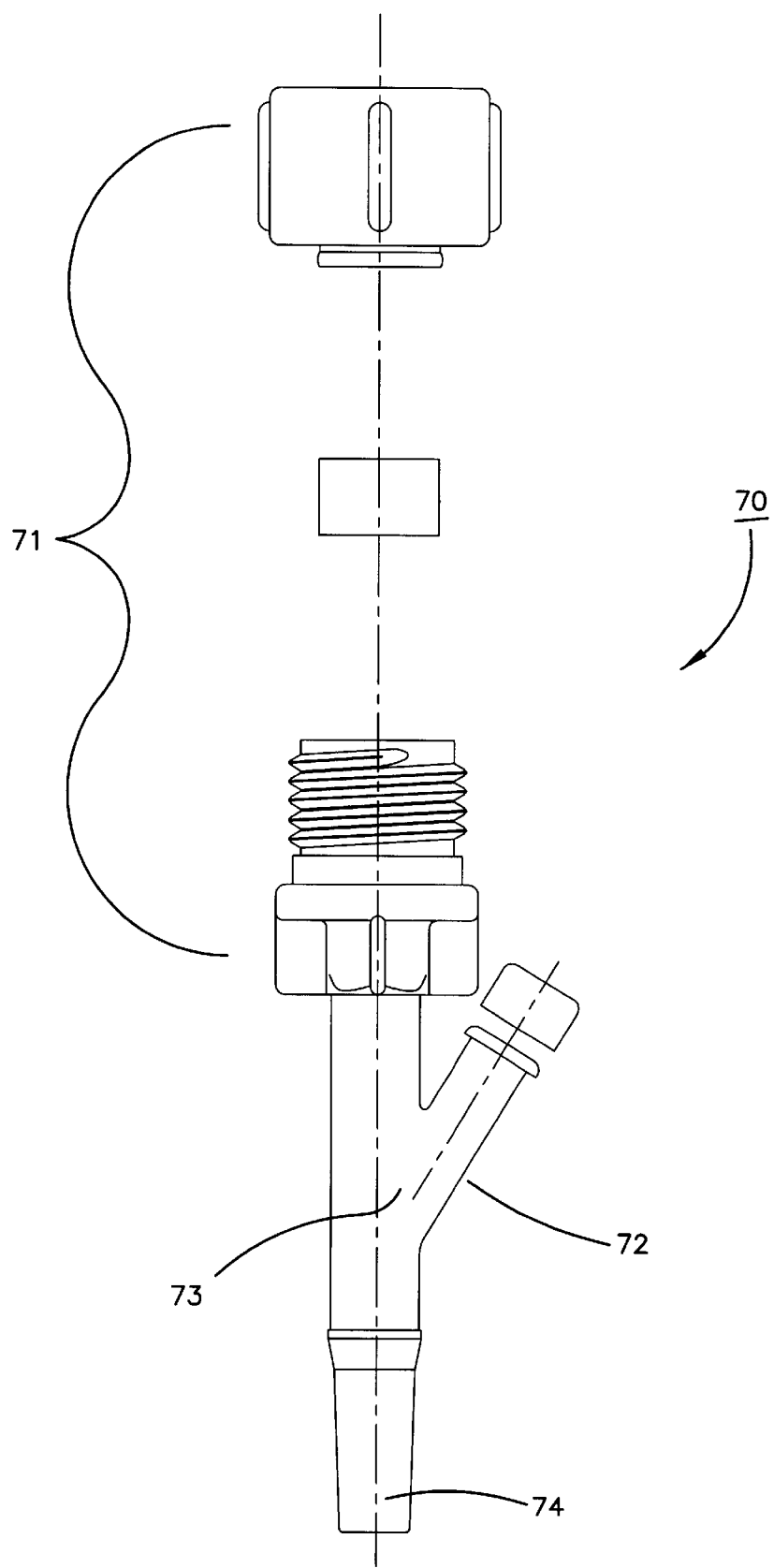
FIG. 9 is an alternative embodiment for a proximal end arrangement for a pericardial access device such as that of FIGS. 1–4.

FIG. 9 illustrates an alternative proximal end arrangement 70. According to this embodiment, a Touhy-Borst valve 71 and a Luer type inlet 72 form a "Y" 73 at the proximal end of the pericardial access device 10. The "Y" embodiment 70 permits material administration or removal via the penetrating body 5 following capture and penetration of the pericardium. That is, the Touhy-Borst valve 71 and Luer inlet 72 meet at a common lumen 74 that communicates with the lumen 9 of penetrating body 5.

Figure 10:
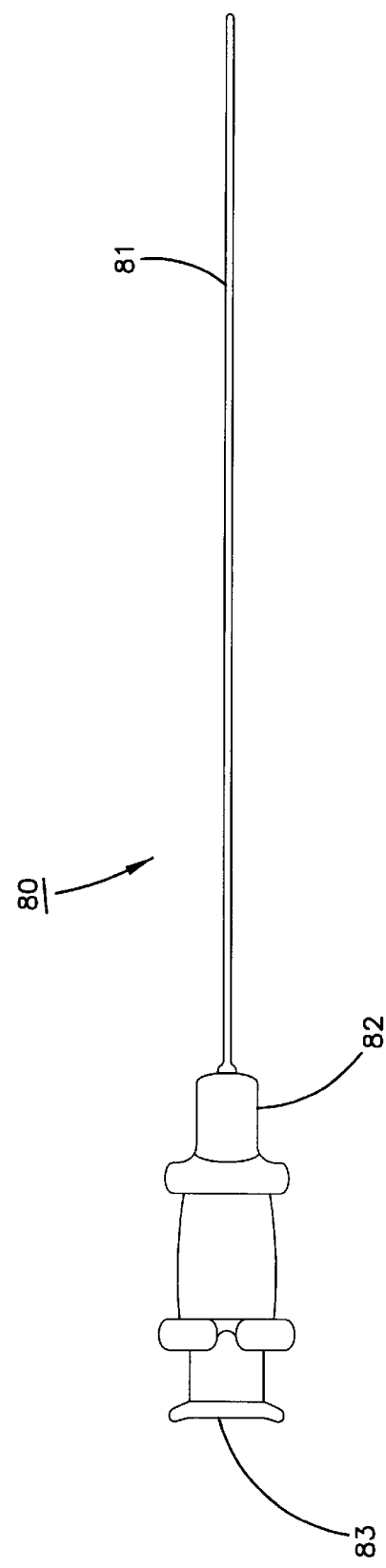
FIG. 10 is an embodiment of a guidewire insertion tool according to the invention.

FIG. 10 illustrates a guidewire insertion tool 80 to facilitate insertion of guidewire 35 into device 10. Referring to FIG. 1, the contours of the inner surface 32 of Touhy-Borst valve 31 are shown in phantom. As illustrated, a shoulder 33 may be present. The shoulder 33 can cause the tip of guidewire 35 to "hang-up" when passed into the guidewire port 23. The guidewire insertion tool 80 prevents the guidewire 35 from hanging up. Specifically, prior to insertion of a guidewire 35 into guidewire port 23, guidewire insertion tool 80 is passed into guidewire port 23. Guidewire insertion tool 80 includes a thinwall blunt end tubing 81 that has an outside diameter of a size sufficient to permit passage into lumen 9 at the proximal end of penetrating body 5. The guidewire insertion tool 80 is passed into the guidewire port 23 until hub 82 is seated within the shouldered inner surface 32 of Touhy-Borst valve 31. The proximal opening 83 of guidewire insertion tool 80 is continuous with blunt tubing 81 and does not have a shoulder or other internal surface contour that can potentially cause the guidewire to hang up. Thus, guidewire 35 can be passed freely without hanging up near the entry of the guidewire port 23.

As discussed below, once guidewire 35 is placed in the pericardial space, the pericardial access device can be removed. a catheter or other known material transport tube can then be guided over the guidewire into the pericardial space. Alternatively, if the guidewire is hollow, materials can be passed directly through the guidewire into the pericardial space.

In addition to cardiac applications disclosed herein, the foregoing access device can also be used for other medical applications. For example, an access device having a suction port in the side wall of the outer tubular body can also be advantageously used to perform procedures within the lumen of a tubular anatomical structure or access structures deep to the surface lining of the tubular anatomical structure when passed into the lumen of the structure. Such tubular anatomical structures include, for example, nasal passages, trachea, bronchi, esophagus, intestine, colon, rectum, ureter, urethra, vagina, uterus, blood vessels, etc. According to this aspect of the invention, for some applications, it may be advantageous for a portion of the outer tubular body and penetrating body to be flexible for selectively conforming the distal end of the device to follow the contours of the tubular organ into which the device is passed. Flexibility of the device can also reduce the chance of trauma to a tubular organ in some circumstances. Flexible materials suitable for the outer tubular body or piercing body include, for example, superelastic metals, plastics, thermoplastic elastomers (TPE), etc.

Figure 25:
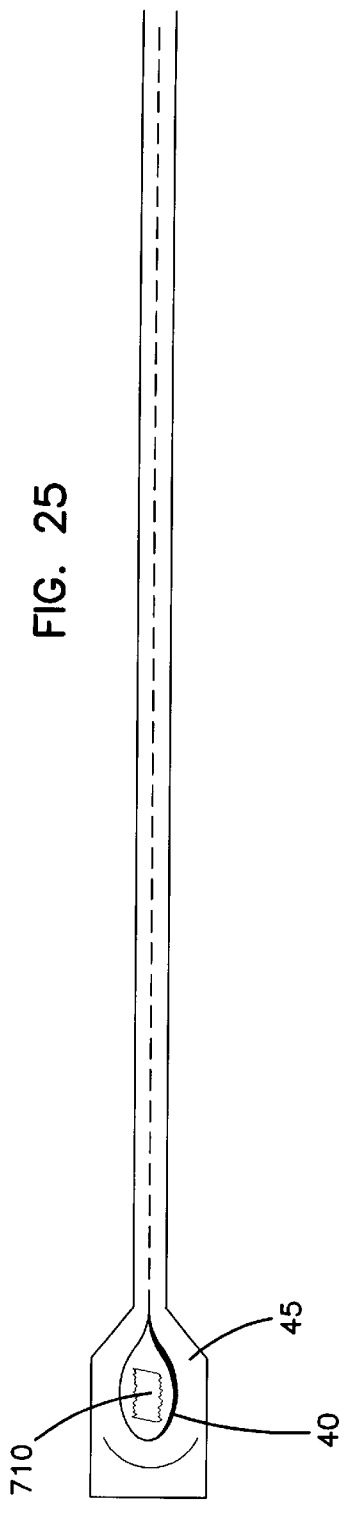
FIG. 25 is a top plan view of the biopsy scoop of the biopsy instrument of FIGS. 24 and 23 as seen through the clear view tube of the pericardial access device of FIGS. 1–4.
Figure 24:
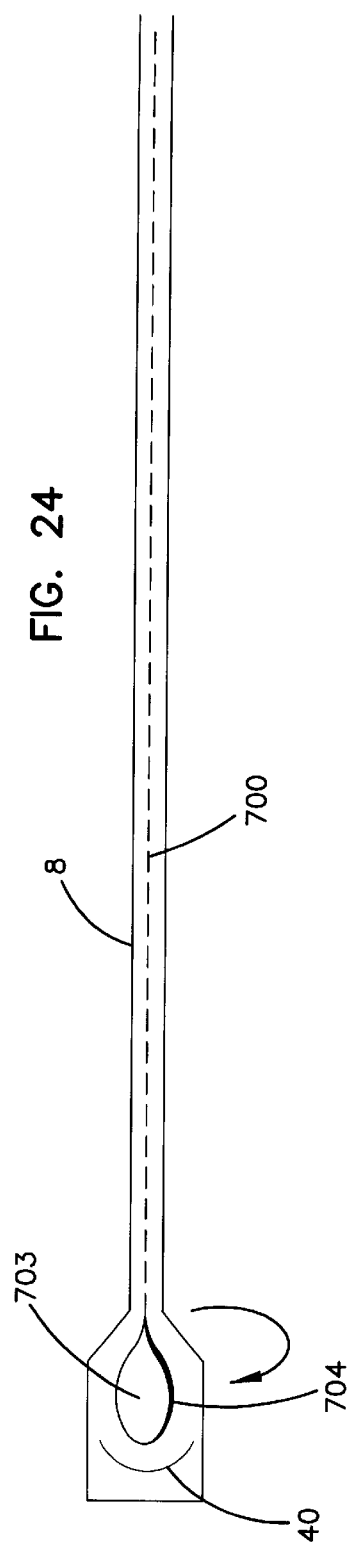
FIG. 24 illustrates the embodiment of the biopsy instrument of FIG. 23 within the lumen of an elongate tubular body of a pericardial access device as illustrated in FIGS. 1–4.
Figure 23:
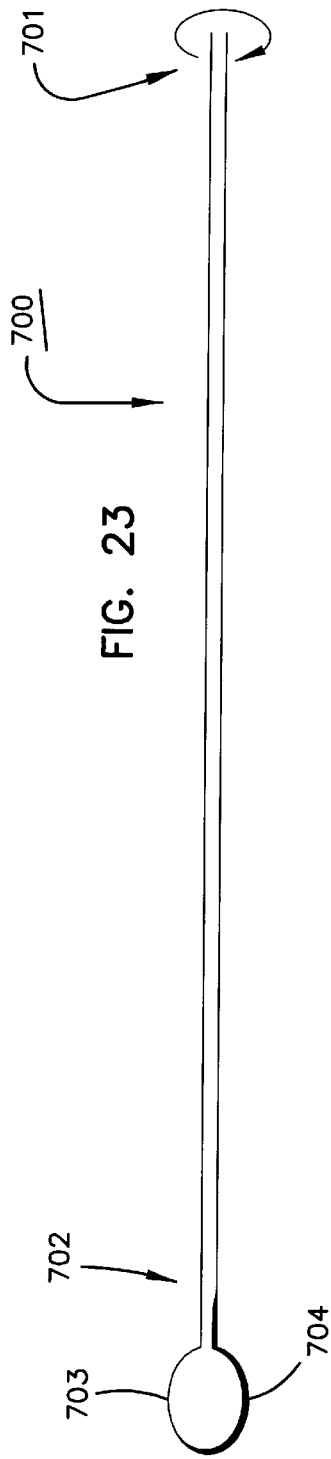
FIG. 23 is an embodiment of a biopsy instrument according to the invention.

Referring to FIGS. 23–25, in another embodiment, the pericardial access device 10 can be configured as a biopsy instrument to take a biopsy sample from the pericardium or other tissue in which the device is passed. According to this embodiment, penetrating body 5 is replaced with a biopsy instrument 700. The biopsy instrument 700 has a proximal end 701 and a distal 702. At the distal end of the biopsy instrument 700 there is a biopsy scoop 703 having a sharp peripheral edge 704 for penetrating and cutting tissue.

During use of the biopsy instrument 700, the pericardial access device 10 is positioned at the surface of the heart as previously described and suction applied to lift a bleb of tissue into depression 40. With the bleb secure in depression 40, the biopsy instrument 700 is advanced distally into the pericardium and rotated (arrow C) via handle arrangement 20 (see eg., FIG. 1) to excise the tissue being biopsied. The excised tissue 710 will be trapped between the scoop 703 and the wall of depression 40 as illustrated in the top view of FIG. 25 looking through clear view tube 45 at the distal end 1 of device 10. The biopsy instrument 700 is then retracted distally into lumen 8 and the pericardial access device 10 removed. The excised tissue sample 710 can then be collected for analysis.

B. Mechanical Grasping Device

In contrast to the pericardial access device described above, the device of U.S. Ser. No. 08/761,189, now U.S. Pat. No. 5,931,810, does not use suction to lift the pericardium away from the heart. Rather, the device lifts the pericardium away from the surface of the heart by mechanically grasping the parietal pericardium and subsequent proximal movement of the device by the operator. Similar to suction devices, a mechanical grasping device can also be used in non-cardiac procedures. Such grasping devices can further include flexible components to conform to the contours of the structure in which the device is used.

Figure 11:
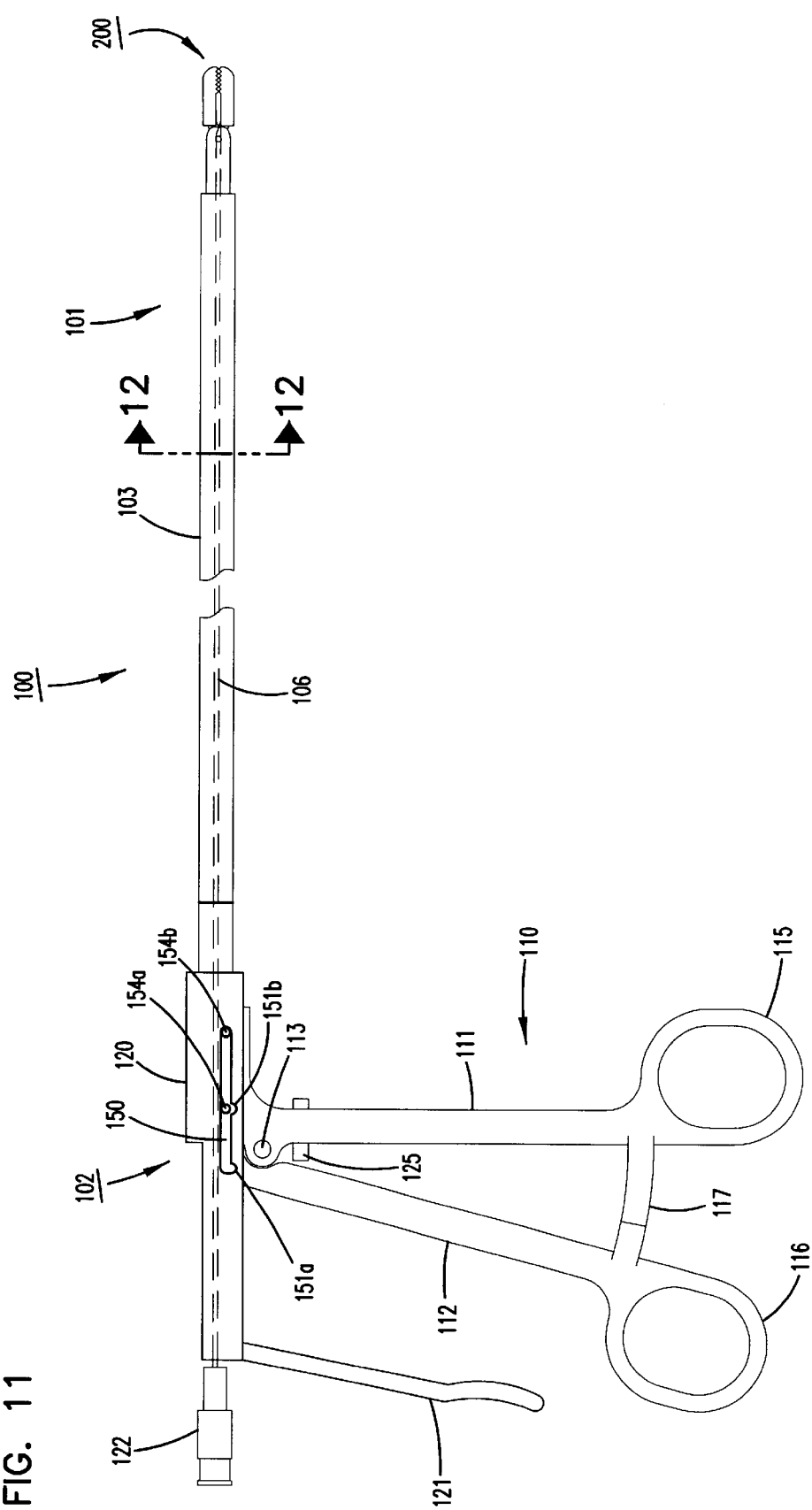
FIG. 11 is a side view of one embodiment of a grasping pericardial access device according to the invention with the jaws closed.
Figure 12:
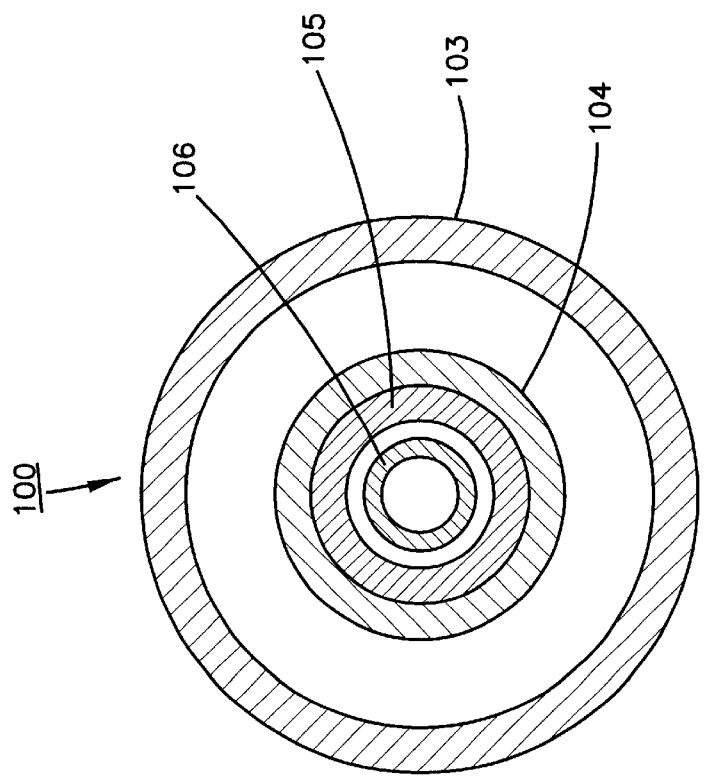
FIG. 12 is a transverse cross section view of the grasping pericardial access device of FIG. 11 taken at 12—12.

Referring now to FIGS. 11–17, one preferred embodiment of a mechanical grasping device 100 for pericardial access will be described. Pericardial access device 100 has a distal end 101 for grasping the pericardium and a proximal end 102 for holding and operating the device 100. FIG. 12 is a transverse cross section view taken at 12—12 of FIG. 11 showing the relative arrangement of structures 103–106. Device 100 includes a tubular outer housing 103, a tubular actuator shaft 104, a penetrating body guide tube 105 and a penetrating body 106.

Figure 13:
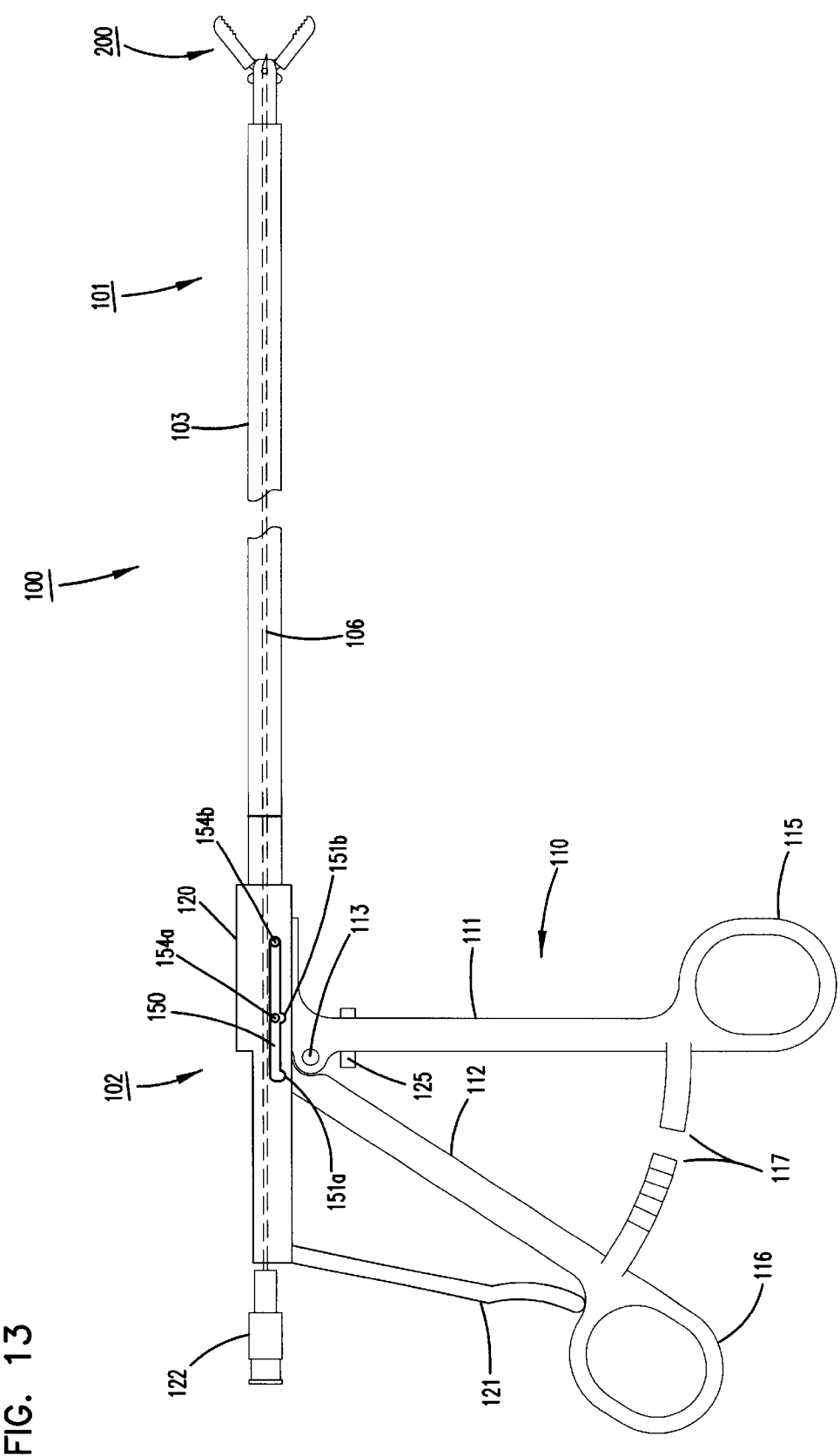
FIG. 13 is the grasping pericardial access device of FIGS. 11 and 12 with the jaws open.
Figure 14:
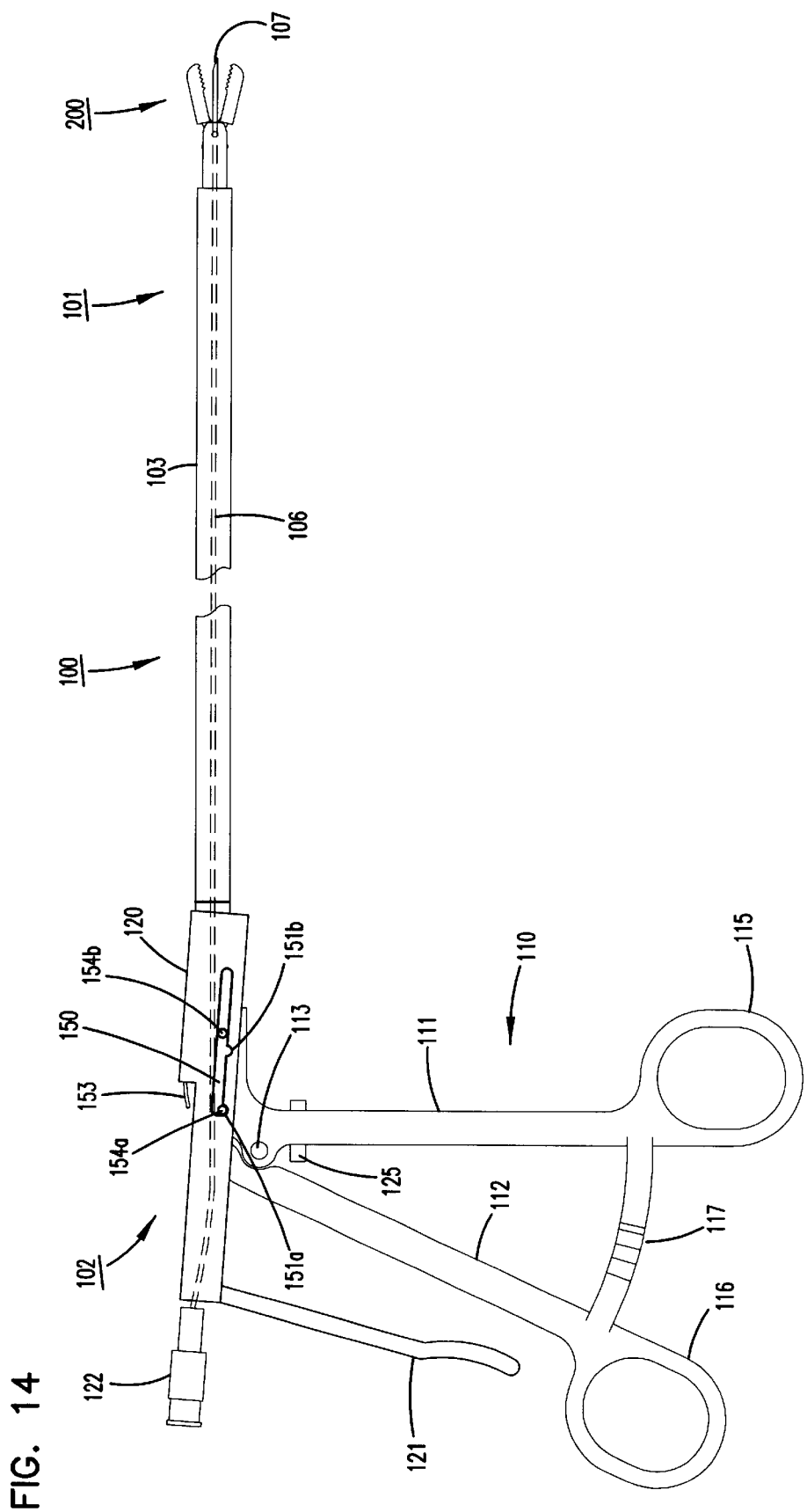
FIG. 14 is the grasping pericardial access device of FIGS. 11–13 with the jaws partially open and the distal piercing end of the penetrating body advanced distally between the jaws.

At the proximal end 102, the access device 100 includes a handle 110 for holding and controlling the grasping function of access device 100 and a carriage 120 for controlling the axial travel of penetrating body 106. FIG. 11 illustrates the relative position of handle arms 111 and 112 of handle 110 when jaws 200 at the distal end of device 100 are closed. FIG. 13 illustrates the position of handle 110 when jaws 200 are fully open and FIG. 14 illustrates the position of handle 110 when jaws 200 are partially open and carriage 120 is distally advanced such that the distal piercing end 107 of penetrating body 106 is distally advanced.

Figure 15:
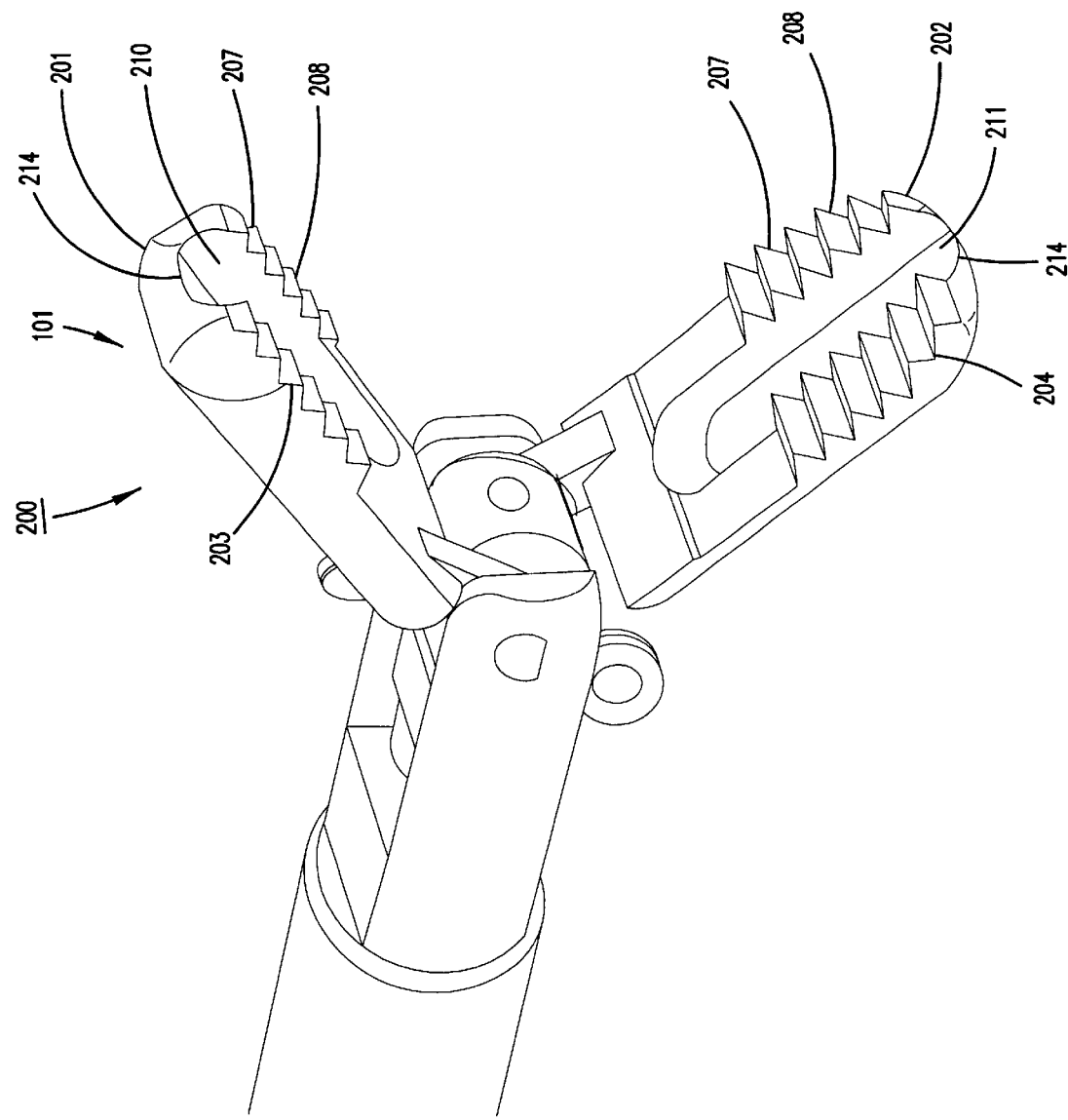
FIG. 15 is a close-up perspective view of a portion of the distal end of the pericardial access device of FIGS. 11–14.

FIG. 15 is a perspective view of distal end 101 of access device 100. As illustrated, jaws 200 include a first grasping element 201 and a second grasping element 202. Each grasping element has a grasping surface 203 and 204, respectively. The grasping surfaces can also include a pattern 207 for facilitating gripping by grasping surfaces 203 and 204. In the illustrated embodiment, the grasping surfaces comprise teeth 208 to grasp and retain pericardial tissue between grasping surfaces 203 and 204. The teeth 208 are preferably of a uniform pitch for the full length of the grasping surfaces 203 or 204 or only for a portion of the length of the grasping surfaces as illustrated in FIG. 15. The teeth 208 could be of different pitches provided they remaining cooperatingly arranged on each grasping surface 203 and 204 and that the grasping surfaces 203 and 204 remain able to close completely.

Grasping surfaces 203 and 204 each also include a longitudinally extending groove 210 and 211, respectively. When jaws 200 are closed, longitudinal grooves 210 and 211 provide a passage that opens at distal tip 214. The passage between grasping surfaces 203 and 204 provides for a material to pass between grasping surfaces 203 and 204 through the passage created by groove 210 and 211 when jaws 200 are closed.

Figure 16:
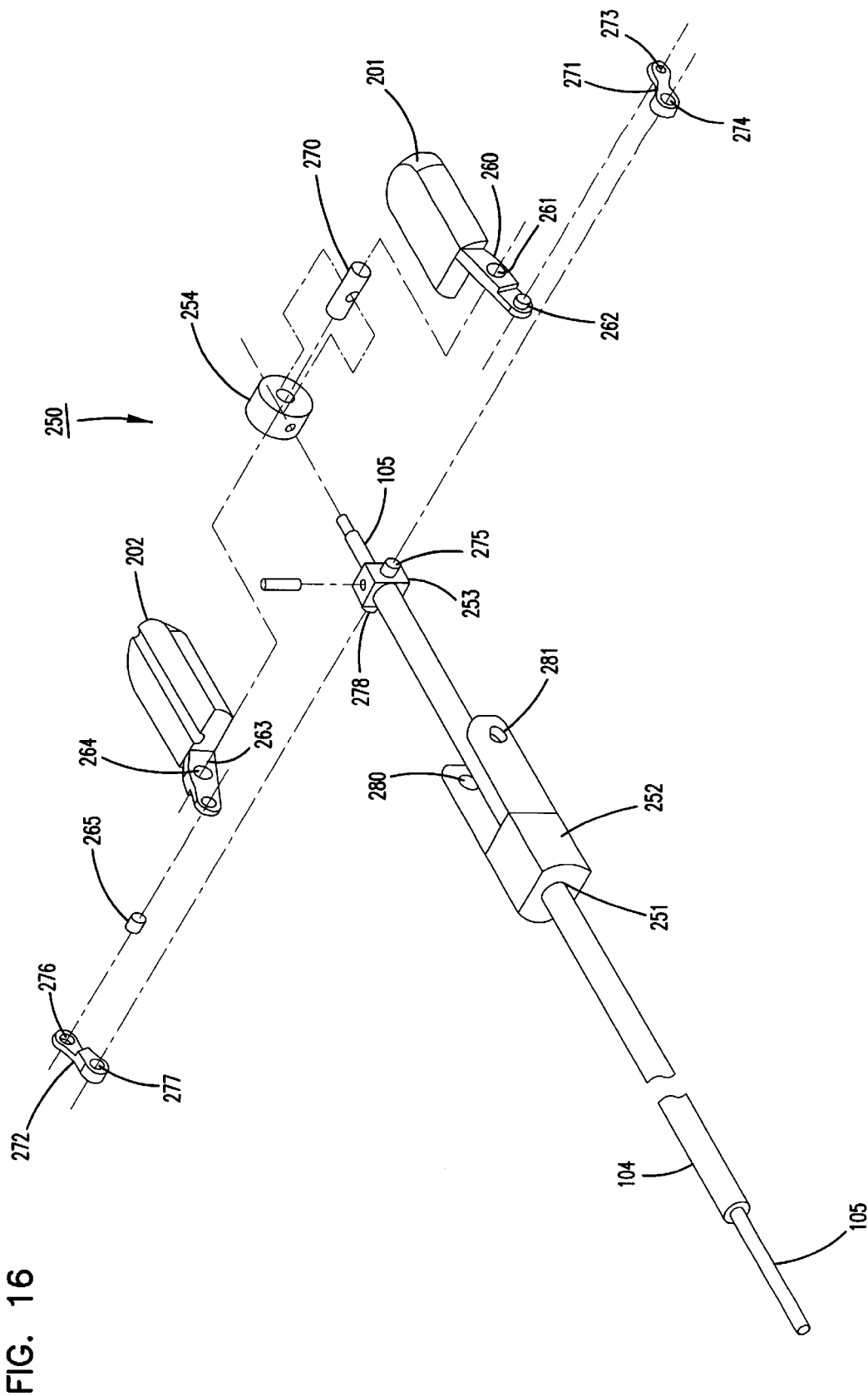
FIG. 16 is an exploded perspective view of the grasping mechanism of the pericardial access device of FIGS. 11–15.

FIG. 16 is an exploded perspective view of the grasping mechanism 250 of pericardial access device 100. For explanatory purposes, outer housing 103 and penetrating body 106 are not shown in FIG. 16. The actuator shaft 104 extends from the proximal end 102 and passes through opening 251 of housing 252 and mounts distally at hub 253. The penetrating body guide tube 105 is axially mobile within actuator shaft 104 and is mounted distally to sleeve 254.

First grasping element 201 includes a first proximal extension 260 having a bore 261 and pin 262. The second grasping element 202 includes a second proximal extension 263 having a bore 264 and pin 265. First grasping element 201 and second grasping element 202 are maintained in spaced apart relationship by sleeve 254 positioned between first and second proximal extensions 260 and 263 and move relative to one another around spindle 270 which passes through sleeve 254, bores 261 and 263 and bores 280 and 281 of housing 252.

Movement of actuator shaft 104 causes the jaws 200 to open and close by transfer of the axial motion of actuator shaft 104 through transfer members 271 and 272. Transfer member 271 includes a distal hole 273 for mounting to pin 262 of grasping element 201 and a proximal hole 274 for mounting to pin 275 of hub 253. Likewise, transfer member 272 includes a distal hole 276 for mounting to pin 265 of grasping element 202 and a proximal hole 277 for mounting to pin 278 of hub 253. Thus, as will be appreciated from the illustrations and foregoing discussion, distal advancement of actuator shaft 104 opens jaws 200 by separating grasping elements 201 and 202 and proximal retraction of actuator shaft 104 closes jaws 200 by moving grasping elements 201 and 202 together.

Figure 17:
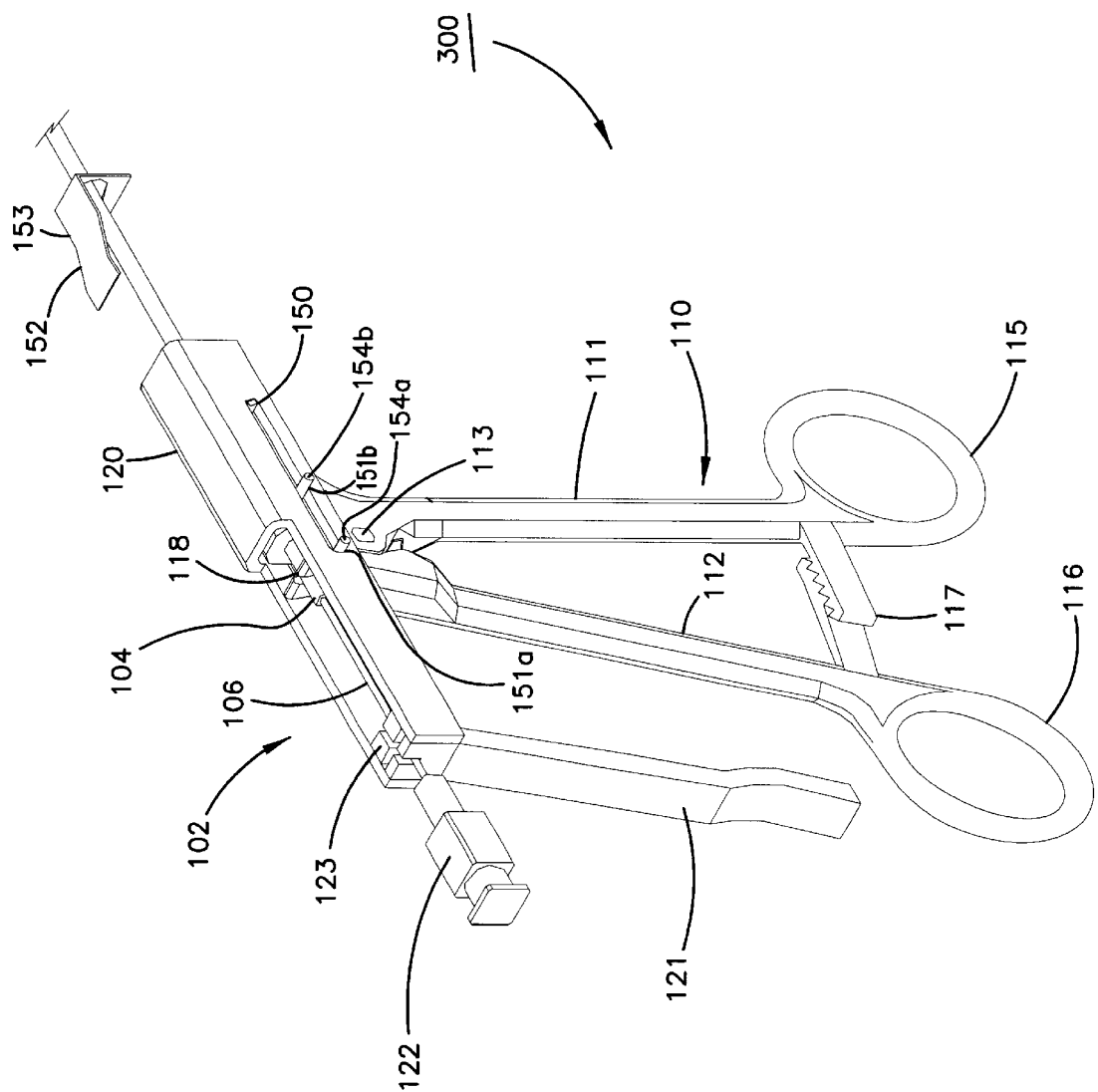
FIG. 17 is a perspective view of a portion of the proximal end of the grasping pericardial access device of FIGS. 11–16.

FIG. 17 illustrates the proximal operating portion 300 of pericardial access device 100. As illustrated, handle 110 comprises fixed arm 111 and moveable arm 112. Moveable arm 112 pivots relative to fixed arm 111 around axis 113. Handle 110 includes finger rings 115 and 116 at arm 111 and 112, respectively. Handle 110 also includes a ratchet locking mechanism 117 which provides for selectively fixing the relative positions of grasping elements 201 and 202. The ratchet locking mechanism 117 advantageously permits the physician to remove his/her hand from handles 111 and 112 without loosing the pericardium or other tissue grasped by the device 100.

Moveable arm 112 is connected to the proximal end 102 of actuator shaft 104 at connection 118 such that moving finger ring 116 distally retracts actuator shaft 104 proximally causing jaws 200 to close. Moving finger ring 116 proximally advances actuator shaft 104 causing jaws 200 to open. Referring to FIGS. 11, 13 and 14, a stop 125 can be positioned between handles 111 and 112 to reduce the chance of inadvertent penetration through the pericardium by grasping surfaces 203 and 204 when jaws 200 are closed.

Carriage 120 provides for selective axial advancement and retraction of penetrating body 106. The proximal aspect of carriage 120 can include a handle 121 for operator convenience in moving the carriage 120. In the illustrated embodiment, the proximal end of penetrating body 106 includes a connector 122 such as a Luer fitting for attachment of a fluid line, a syringe, etc., to the proximal end of the penetrating body 106. The proximal end 102 of penetrating body 106 is firmly connected to the carriage 120 by fixing arrangement 123.

Carriage 120 also includes cut out groove 150 having notches 151a and 151b. Bias mechanism 152 is illustrated outside of carriage 120. However, when assembled, bias mechanism 152, such as a spring clip 153, is located within the proximal aspect of carriage 120 (see FIG. 14) and functions to bias carriage 120 upward causing notches 151a or 151b to interdigitate with pins 154a or 154b (FIG. 13) to secure carriage 120 in a selected position. In the illustrated embodiment, the opposite side of carriage 120 includes an identical arrangement of pins 154a and 154b, notches 151a and 151b and cut out groove 150. Pushing carriage 120 down to overcome the upward bias of spring clip 153 causes notches 151a or 151b to move from pins 154a or 154b and permits proximal and distal movement of carriage 120 for retraction and advancement of penetrating body 106. The proximal aspect of groove 150 limits distal advancement of penetrating body 106.

In use, carriage 120 can be retracted proximally and the access device 100 passed through a minimally invasive incision in the chest wall to the heart. Jaws 200 are then opened and the parietal (outer) pericardium grasped between the jaws. The device 100 is then carefully pulled in a proximal direction to lift a portion of the grasped parietal pericardium away from the surface of the heart. Subsequently, carriage 120 is moved distally to advance the piercing distal end 107 of penetrating body 106 into the pericardial space. A guidewire can then be passed through the penetrating body into the pericardial space and access device 100 removed.

Once the pericardial space is accessed, a guidewire can be passed through penetrating body 106 into the pericardial space and the access device removed. In some procedures, a material transport tube can be passed over the guidewire into the pericardial space and the guidewire removed. A material transport tube of the invention provides for passing a material into the pericardial space. As used herein, "material" includes anything that can be introduced into the pericardial space through the material transport tube including gasses, liquids or solids. Thus, "materials" include pharmacological agents (e.g., vasodilators, antiplatelets, anticoagulants, thrombolytics, anti-inflammatories, antibiotics, fibrinolytics, antiarrhythmics, inotropics, antimitototics, angiogenics, antiatherogenics, and any other suitable compound, for example, as described in PCT Publication WO 97/16170) heated or cooled fluids (e.g., ice water), saline solutions, flowable powders, controlled drug release implants, or other solid materials including, for example, implantable devices, diagnostic and therapeutic instruments, surgical instruments, electrical leads, etc. As used herein, a "material transport tube" includes known catheters, trocars, hollow guidewires, or other similar devices that serve as a conduit for delivery or removal of a material to or from a site.

In some embodiments, the guidewire can also function as a material transport tube. That is, in some embodiments, the guidewire may be hollow and provide for material transport through the guidewire to a selected site. The hollow guidewires can be open at the distal tip for distal delivery or along the sidewalls for side delivery of a material. Alternatively, a material transport tube can be passed through a hollow guidewire rather than over the guidewire.

Figure 18:
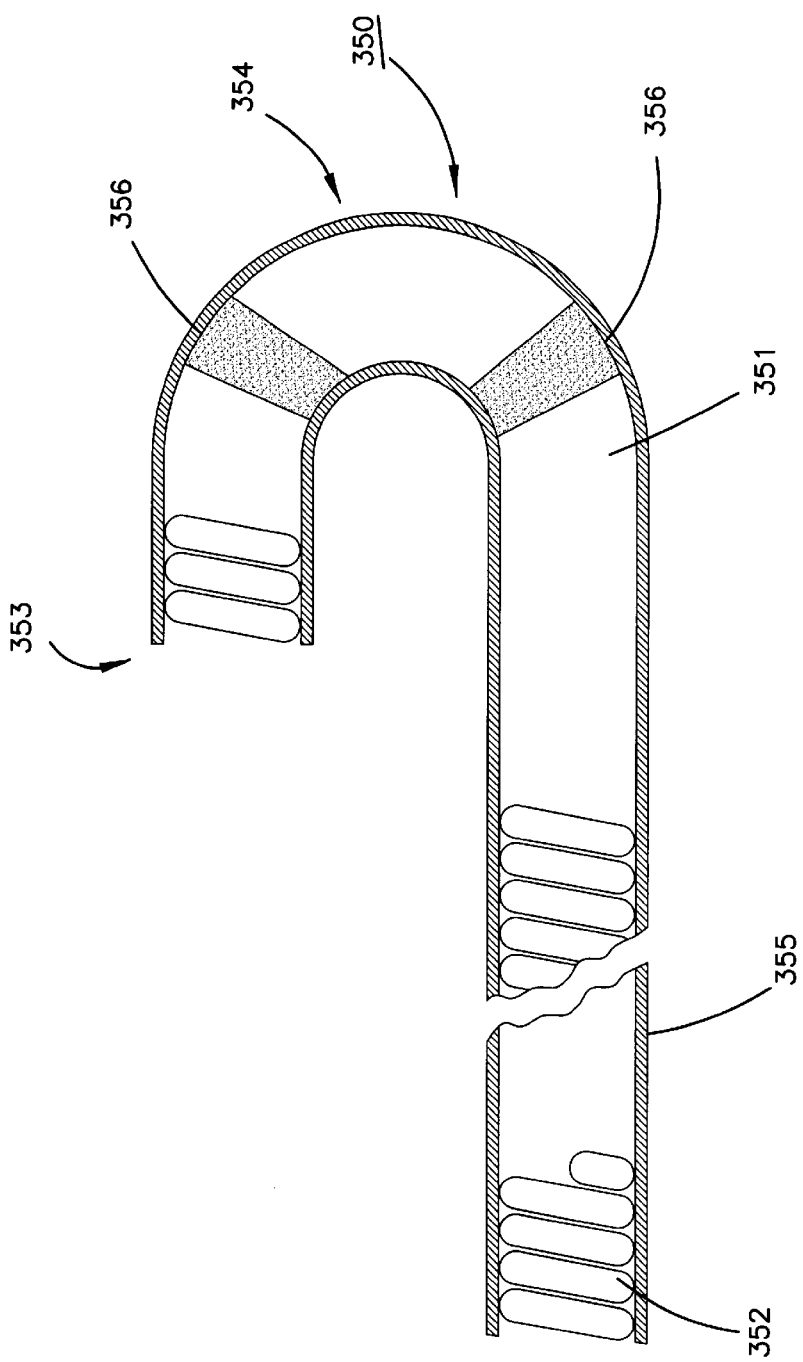
FIG. 18 is a side view of the distal end of an open-ended infusion wire according to the invention.

Hollow (infusion) guidewires are known. In one embodiment a hollow guidewire can be open-ended infusion wire 350 as illustrated in FIG. 18. The open-ended infusion wire 350 combines the functions of a solid guidewire and a material transport tube. According to the illustrated embodiment, the infusion wire 350 includes a lumen 351 surrounded by coiled wire 352. The coiled wire can be manufactured from known materials including, stainless steel, nitinol, titanium, nickel-titanium, etc. The coiled wire 352 can extend the length of the infusion wire 350 and can be coated 355 along the entire length to prevent a fluid in the lumen from passing out of the lumen. Preferably, the coating does not prevent the infusion wire 350 from sliding freely when passed through the lumen of a penetrating body. Suitable coatings 355 include, for example, PTFE, polyurethane, polyethylene, a lubricious layer (e.g., silicon or other hydrophilic material), or other material which decreases friction.

In the illustrated embodiment, the distal end 353 of the infusion wire 350 can include a "J" or modified "J" configuration 354. This J shaped 354 distal end provides for advantageous functions such as: (1) easy exit of the infusion wire 350 from the penetrating body, for example, by reducing the chance of impinging on the distal wall 120 of depression 40 when exiting a pericardial access device 10; (2) protection of the pericardial surface; and (3) holding the guidewire in place in the pericardial space. The J shape is preferably formed from a shape memory material to provide for straightening of the J curve during passage through a linear body and recurvature upon exiting. Shape memory materials that are shape responsive to temperature changes can also be advantageously used.

In one preferred embodiment of an infusion wire, for example for use with a penetrating body having an inside diameter of about 0.023 inch, the infusion wire can have an outer diameter of about 0.016 to 0.020 inch, typically about 0.018 inch and an inner diameter of about 0.006 to 0.010 inch, typically about 0.008 inch. The overall length of an infusion wire 350 can be about 50 to 150 cm, typically about 100 cm and can withstand an infusion pressure of at least 250 psi. In some embodiments, the infusion wire can include one or more radiopaque markers 356 along the length of the wire 350 for visualization under fluoroscopy or x-ray. In some embodiments, the radiopaque marker may be located only at the distal tip. In other embodiments, the markers may be non-radiopaque for visualization outside of the patient's body.

At the proximal end (not illustrated), the infusion wire 350 can include known assemblies for operating or manipulating the wire. In addition, the proximal end of the infusion wire 350 can include, an arrangement for attaching a fluid dispensing system, Touhy-Borst valve, etc. The infusion wire 350 can be included in a kit with a pericardial access device as discussed further below.

Preferably, the distal end of the infusion wire 354 is sufficiently supple to be easily removed from the pericardium upon the completion of a procedure without trauma to the patient or tissues. In addition, it may be advantageous to shorten the coating 355 and leave about 2–3 centimeter of the coiled wire 352 uncovered at the distal end of the J shape to soften the tip feel or facilitate removal. Generally, the infusion wire 350 will be passed through the lumen of the penetrating body from the proximal to distal end. Accordingly, the J configuration should be of a shape memory material permitting straightening during passage through the penetrating body lumen and returning to the J shape once passed outside the distal end of the penetrating body.

In some embodiments, a material such as a medical instrument can be passed into the pericardial space without the use of a material transport tube. For example, rather than passing a material transport tube over the guidewire and subsequently passing the instrument through the transport tube, the instrument can be manufactured to include a guiding lumen (e.g., a monorail). The guiding lumen can extend along the length of instrument or be located only at the distal end and function as a track that passes over the guidewire for guiding the instrument into the pericardial space.

The present invention also provides kits including some or all components necessary to perform a particular medical procedure. Thus, in one embodiment, a kit can include a pericardial access device and a guidewire. The kit can also include an introducer and/or introducer guidewire for placement of the pericardial access device. Suitable introducers are known and include, for example, a single piece blunt end cannula, a dilator with attached sheath, a longitudinally splitable sheath, etc. In some embodiments, a kit can further include a material transport tube for passing a material into the pericardial space. In other embodiments, a kit can include a pericardial access device and an instrument for performing a diagnostic or therapeutic procedure. According to this embodiment, the kit can also include a guidewire and material transport tube for passing the instrument into the pericardial space. Permutations of groupings of a pericardial access device, material transport tube, guidewire, medical instruments or other component which are combined for purposes of providing the clinician with preferred components for performing a particular medical procedure will be appreciated as a kit within the scope of the invention.

The pericardial access procedures disclosed herein can be used to provide access to the pericardial space through an outside-in approach, to perform known procedures in the pericardial space. In addition, the invention provides new and advantageous methods for performing minimally invasive diagnostic and therapeutic cardiac procedures in the pericardial space.

II. Drug Delivery

The devices and methods of the invention can be used to deliver a pharmacological agent directly to the pericardial space. The delivery of a pharmacological agent directly to the pericardial space is described in, for example, U.S. Pat. No. 5,269,326, U.S. Pat. No. 5,681,278 and PCT Publication WO 97/16170 the disclosures of which are incorporated herein by reference. As used herein, a "pharmacological agent" or "drug" refers to any exogenous or endogenous substance that provides a diagnostic, therapeutic or palliative effect to the body and particularly the heart. Administration of a pharmacological agent to the pericardial space provides for advantageous delivery of the agent to coronary muscles, vessels or other structures without distribution to other organs of the body.

The devices and methods of the invention can be used for short term or long term ("chronic") drug delivery to the heart. Long term delivery can be provided through the use of known catheter systems placed in the pericardial space using the devices or methods of the invention. The distal end of a suitable drug delivery catheter can include single or multiple lumen catheters having one or more openings through which a material passed into the catheter can enter the pericardial space. The proximal end of the catheters can be constructed for attachment to externally located syringes, infusion pumps, etc. The proximal end of the catheters can alternatively be attached to infusion systems which can be implanted or otherwise attached to the patient.

In addition, long term treatment of the heart can be provided according to the invention through the use of "controlled drug release systems." Such controlled release systems include controlled administration of free drug and sustained and delayed drug release systems. In one embodiment controlled drug delivery to the surface of the heart can be provided by a drug release patch such as disclosed in U.S. Pat. No. 5,387,419. As used herein, a controlled drug release system also includes iontophoretic delivery of a pharmacological agent to the surface of the heart. Such systems are disclosed in, for example, U.S. Pat. Nos. 5,087,243 and 5,634,895. In another embodiment, a controlled drug release system can include a biodegradable implant capable of controlled drug release as disclosed in, for example, U.S. Pat. No. 5,681,278. The entire disclosures of each of these patents are incorporated herein by reference. The patents disclosed are provided as examples of the scope of controlled drug delivery systems suitable for use according to the invention and are not intended to limit the invention in any way.

The invention further provides kits for applying a drug delivery system into the pericardial space. For example, a kit can include a pericardial access device and a controlled drug release system. The kit can also include a guidewire, material transport tube or other component to facilitate a particular application of the drug delivery system.

Figure 19:
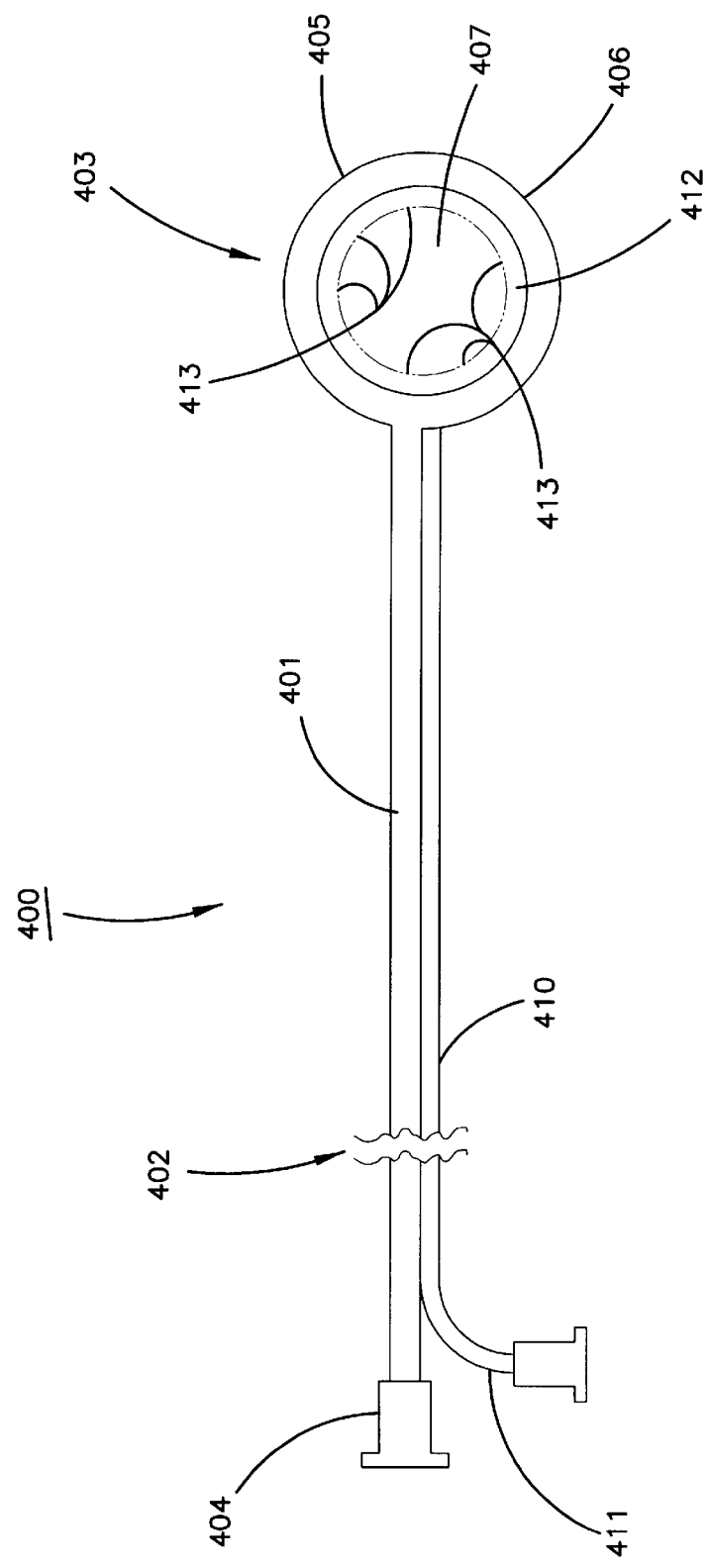
FIG. 19 is a top view of one embodiment of a local administration apparatus according to the invention.

In another embodiment, the invention provides a "local administration apparatus" for administering a pharmacological agent to a localized region of the heart. One such embodiment of a local administration apparatus is illustrated in FIG. 19. As illustrated, the local administration apparatus 400 can include a first lumen 401 having a proximal end 402 and a distal end 403. The proximal end 402 can include a connector such as a Luer connector 404 for providing a fluid (liquid or gas) to inflate a balloon 405 at the distal end 403. In the illustrated embodiment, the distal end balloon 405 is "donut" shaped 406 and includes a hole 407 within the donut 406 for maintaining a material within. That is, when the local administration apparatus 400 is passed into the pericardial space and applied to the surface of the heart, a diagnostic imaging fluid, drug or other material can be passed into the hole 407 and will generally remain localized within the hole 407. It will be appreciated that while the shape of the illustrated embodiment of the distal end balloon is circular, it can alternatively be any shape suitable for the particular procedure including, rectangular, square, triangular, trapezoidal, etc.

The apparatus 400 can also be used to perform procedures such as aspirating fluid from the surface of the heart to create a dry procedural field. The apparatus can also be used to "anchor" the catheter at a specific location of the heart to which other instruments are passed such as sensors, electrodes, x-ray emitters, tools for destroying vascular obstructions such as plaque, etc.

In use, a separate catheter (not illustrated) can be passed into the pericardial space between the epicardium and balloon 405 or between the pericardium and balloon 405 for dispensing the material into the hole 407 of the balloon 406. Alternatively, the local administration apparatus 400 can include a second lumen 410 having a proximal end 411 for administering a material into the second lumen 410 and a distal end 412 having one or more openings 413 that open into the hole 407. One or more additional lumens can be also be provided for passing over a guidewire into the pericardial space or dispensing other materials to the pericardial space.

II. Diagnostic Image Enhancing Agents

The devices and methods of the invention can also be used for dispensing a diagnostic imaging agent into the pericardial space. A diagnostic imaging agent includes known agents such as a radio-labeled or echo-sensitive dye.

III. Electrophysiology

Invasive electrophysiological studies are used to investigate the mechanisms of arrhythmia. The procedure requires placement of electrodes in the heart for recording intracardiac electrocardiograms ("ECG"). By placing the electrode of an electrophysiology catheter in close proximity to the heart, more detailed information about the electrical activity within the heart can be obtained than from a surface ECG. An electrophysiology study may provide determination of the cause, location, differentiation or treatment of arrhythmia's including atrial fibrillation, atrial flutter, ventricular arrhythmias, atrial-ventricular (AV) conduction delays or blocks, and paroxysmal supraventricular tachycardia (PSVT).

Two significant heart rhythm disorders amenable to electrophysiology technology are atrial fibrillation (AF) and ventricular tachycardia (VT). Treatment of AF and VT via electrophysiology methods include diagnosing the source of the arrhythmia by locating its origin ("mapping") and restoring normal heart rhythms by isolating or destroying the arrhythmia causing sites ("ablation").

Ablation is typically used to destroy arrhythmia causing tissue by freezing, burning or surgical removal. Earlier ablation methods for treatment of cardiac arrhythmias has relied on creating scalpel incisions to interrupt a reentrant circuit using the invasive Cox-Maze procedure. More recently, catheter ablation techniques have been developed. These techniques involve positioning a catheter inside the heart at an arrhythmogenic focus or conduction defect and delivering energy or other arrhythmogenic destroying modality. Such arrhythmogenic destroying modalities include, for example, radiofrequency energy (RE), high energy direct current (DC), microwave energy and laser energy as well as thermal (freezing) or chemical (e.g., ethanol) destruction. Presently, RF energy is a popular method for RF ablation.

Electrophysiology catheters suitable for mapping, ablating, or both are known. Diagnostic (mapping) electrophysiology catheters are presently available from, for example, Bard, Cordis-Webster Laboratories, Boston Scientific, CardioRhythm, Arrow, Daig and Cook Cardiology. Presently, there are no approved products for catheter ablation. However, companies developing products in this area include, for example, CardioRhythm and companies developing catheters that both map and ablate include, for example, Cardima, Osypka, and VascoMed.

Generally, electrophysiology procedures are performed by mapping and ablating arrhythmia causing tissue from the endocardial surface of the heart. For atrial fibrillation, transmucosal lesions may be created in the atrial wall. The majority of the monomorphic sustained VT's are believed to originate from a reentrant circuit located at the subendocardium. See e.g., Edwardo Sosa et al., "A New Technique to Perform Epicardial Mapping in the Electrophysiology laboratory," *Journal of Cardiovas. Electrophys.*, 7(6) :531–536 (June 1996). However, it is estimated that essentially all VT circuits have a myocardial or epicardial component. In some patients, VT may result from subepicardial macroreentry. Id. Thus, the differentiation between an epicardial and endocardial circuit is necessary. Techniques for epicardial mapping have been suggested. See eg., Id. Ablation of the epicardial surface of dogs through an open thoracotomy approach has also been disclosed. K. Hirao et al., "Electrophysiology of the Atrio-AV Nodal Inputs and Exits in the Normal Dog Heart: Radiofrequency Ablation Using an Epicardial Approach," *J. of Cardiovas. Phys.*, 8(8):904–915 (August 1997).

The present invention provides devices and methods for minimally invasive access to the pericardial space for performing epicardial mapping and ablation procedures. Once the pericardial space has been accessed as disclosed herein, a material transport tube can be placed into the pericardial space and an electrophysiology catheter passed through the material transport tube (e.g., catheter) into the pericardial space. Alternatively, an electrophysiology catheter can include a separate lumen for following a guidewire placed in the pericardial space. Once in the pericardial space, mapping or ablation of the epicardial surface can be advantageously performed without obstruction from, for example, septal walls, valves, chordea tehdouae, etc., which can occur using an endocardial approach.

As discussed, arrhythmia causing tissue involved in AF and VT or other arrhythmia can be located on the endocardial surface of the heart, the epicardial surface or in the myocardium. Thus, the present invention foresees the use of minimally invasive epicardial mapping and/or ablation procedures combined with traditional endocardial mapping and/or ablation procedures to effectively localize and destroy the aberrant electrical tissue. According to the invention, an endocardial procedure can be followed by an epicardial procedure or alternatively, an epicardial procedure can follow an endocardial procedure. Diagnosis and treatment of localized arrhythmogenic foci will be more effectively treated by the herein described minimally invasive "two surface" procedure.

Often times, positioning a mapping or ablation catheter at a desired site can be difficult. According to the present invention, in one embodiment, a catheter for mapping or ablation (or both if combined in one catheter) can include an inflatable balloon located proximal to the diagnostic electrodes or ablation arrangement of a steerable catheter. The balloon advantageously provides easier manipulation of the distal tip of the catheter in the pericardial space.

Figure 20:
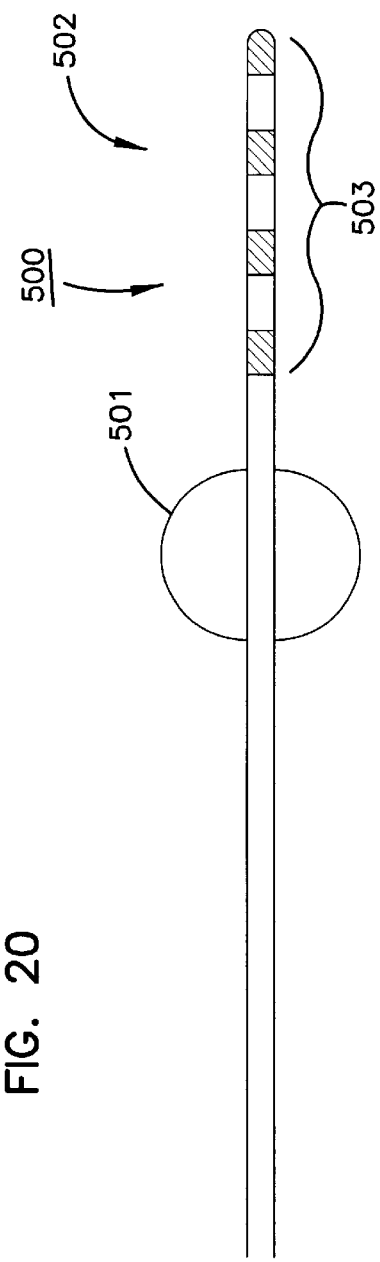
FIG. 20 is an embodiment of an electrophysiology catheter including a dilated balloon according to the invention.

Referring to FIG. 20, one example of a steerable electrophysiology catheter with greater manipulatability is shown.

The catheter 500 is illustrated with a distended balloon 501 located at the distal end 502, proximal to the distally located working area 503 of the catheter. According to the illustration, the working area 503 can include a diagnostic electrode for mapping and/or an energy, chemical or thermal emitting arrangement for tissue ablation. The catheter also includes known technology for steering the distal end 502. Locating balloon 501 proximal to the working area 503 of the distal end 502 enhances the ability to position the working area 502 of the catheter at a selected location within the pericardial space. In use, once the catheter 500 is placed into the pericardial space, the balloon 501 can be distended to separate the pericardium from the epicardial surface of the heart. This separation provides an increased procedural field for the distal end 502 of the catheter to be rotated for mapping or ablating the epicardial surface of the heart with reduced chance of interference by the overlying pericardium. In addition, the balloon can help prevent the catheter from inadvertently being pulled from its location in the pericardial space.

Figure 21:
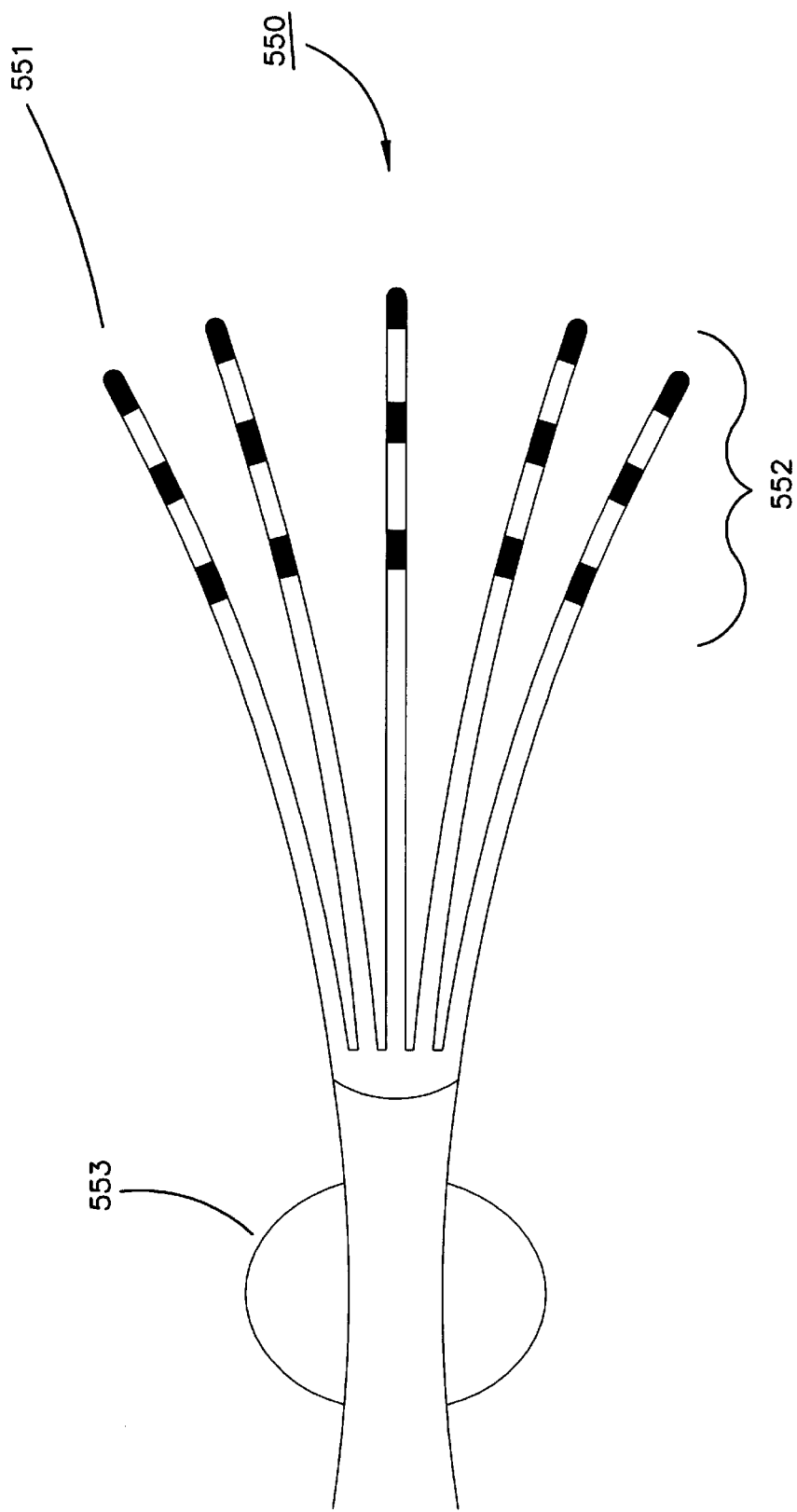
FIG. 21 is an embodiment of a multiprobe electrophysiology catheter according to the invention.

Thus, a kit according to the present invention also can include a pericardial access device including one or more of a guidewire, material transport tube, electrophysiology mapping catheter, ablation catheter or both. Referring to FIG. 21, the present invention also foresees a multiprobe electrophysiology mapping and/or ablating catheter. As illustrated, multiprobe catheter 550 can include a plurality of probes 551, each having a working area 552 including a diagnostic electrode and/or ablation arrangement. Each probe 551 will be independently steerable and provide for simultaneously taking multiple readings of electrical activity of the epicardial surface of the heart. The catheter 500 can also include a balloon 553 proximal to the working area 551 as described above.

IV. Angioplasty

Coronary artery disease is characterized by the progressive accumulation of plaque, etc. which narrows the coronary artery and reduces blood flow to the heart muscle. Coronary artery bypass graph surgery ("CABG") has been shown to be a highly effective method for treating coronary artery disease. However, a known alternative therapeutic procedure for coronary artery disease is percutaneous transluminal coronary angioplasty ("PTCA") which involves passing a small balloon catheter into an obstructed or narrowed region of a coronary artery and inflating the balloon to effectively dilate the narrowed region.

In another embodiment, the devices and methods of the present invention also provide a pericardial approach for performing a balloon angioplasty procedure in a coronary vessel. According to this embodiment, the angioplasty catheter is inserted into a small incision made in the coronary vessel at a location proximal or distal to the narrowing obstruction. The balloon is passed into the narrowed region and inflated to dilate the obstruction using known methods. After completion of the dilation procedure, the angioplasty catheter can be removed from the coronary vessel and the site of entry into the vessel closed. Using a pericardial access approach to angioplasty can provide greater control and precision of placement of the balloon relative to the lesion due to the shorter path the angioplasty catheter must travel to the lesion as compared to catheter entry through a peripheral artery. In addition, other instruments for destroying a coronary vessel blockage, such as ultrasound or other energy source can be passed through a pericardial access device for treatment of the lesion from the exterior of the vessel.

V. Stents

The use of a radioactive or non-radioactive stent at the site of a narrowing obstruction of a coronary vessel for the treatment of coronary artery disease is known. In another embodiment, the pericardial access procedures disclosed herein further provide a new method for minimally invasive access to the coronary vasculature for insertion of a stent, or a coronary artery bypass graft.

As described above for balloon angioplasty, once the pericardial space is accessed, an entry site is made into the diseased artery at a location proximal or distal to the site of narrowing. The stent is passed into the artery through the entry site to the region of obstruction and the stent is implanted using known methods. The site of entry into the coronary vessel can be closed using known methods.

VI. Restenosis

A major limitation to the use of angioplasty when compared to coronary by-pass surgery is the restenosis which can occur post angioplasty. Therapeutic methods to reduce restenosis after coronary angioplasty using ionizing radiation are known. Such methods typically involve endovascular delivery of ionizing radiation to the angioplasty site in the form of beta, gamma or x-ray irradiation. Devices for restenosis reduction are available from, for example, Novoste Corp., Guidant, Neocardia, Nucleotron and XRT Corp. Cook Cardiology, Isostent and Pharmacyclics.

The devices and methods disclosed herein advantageously provide new procedures for accessing a coronary artery for restenosis reduction. According to this aspect of the invention, known systems for providing ionizing radiation to the endothelial surface of a coronary vessel can be applied directly to the outer surface of a coronary artery through the pericardial space using a pericardial access device or method as disclosed herein. Kits can be prepared including a pericardial access device and an ionizing radiation emitting catheter. In addition, the kits can also include a guidewire, material transport tube, or other instrument to facilitate restenosis reduction through a pericardial approach.

It is foreseen that pharmaceutical agents effective in the treatment of restenosis can also be administered to an affected vessel according to the methods of the invention.

VII. Pericardial Procedural Field

As will be appreciated from the foregoing discussion, the pericardial access procedures of the present invention provide pericardial access for performing various cardiac procedures through a pericardial approach. In addition to providing an exterior approach to the coronary vasculature for electrophysiology mapping and ablation, transluminal angioplasty, angiography, stent placement, graft placement, etc. it will be appreciated that many other procedures can be performed from the pericardial space.

Thus, in another embodiment, the present invention facilitates performing a procedure in the pericardial space by providing a "pericardial procedural field." According to this embodiment, a procedural field is created in the pericardial space by dilating the outer (parietal) layer of the pericardium from the epicardial surface after the pericardial space has been accessed. Pericardial dilation can be performed by passing a physiologically acceptable fluid, including known gasses and liquids into the pericardial space. In a preferred embodiment, the fluid is passed into the pericardial space into a balloon at the distal end of the catheter. One or more balloons of varied size or shape can be inserted into the pericardial space and selectively positioned to create a procedural field for performing a diagnostic or therapeutic procedure between the balloons.

Figure 22:
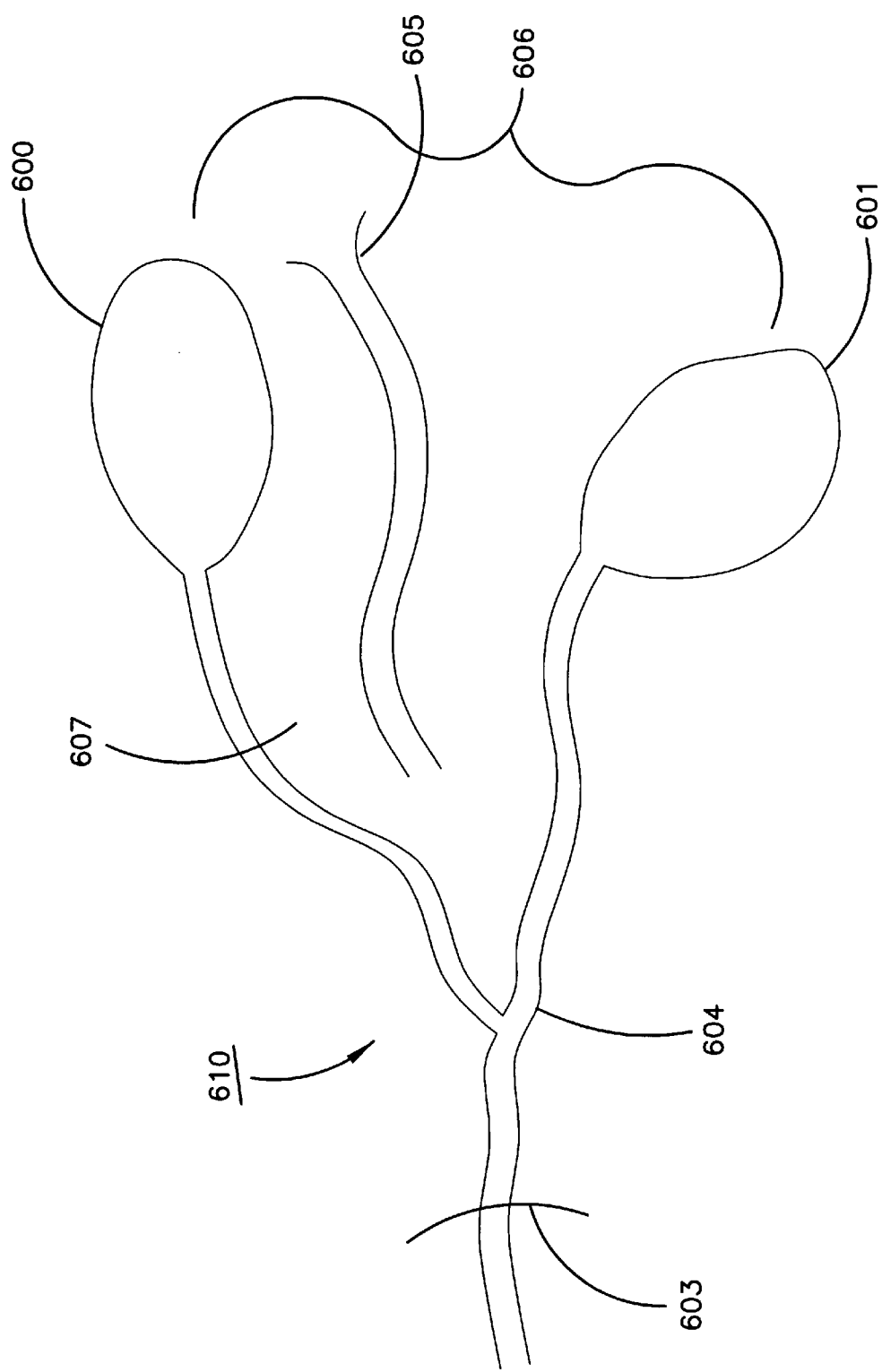
FIG. 22 is a top view of a device for creating a procedural field in the pericardial space according to the invention.

For example, FIG. 22 diagrammatically illustrates a pericardial procedural field device 610 including placement of two balloons 600, 601 through an opening 603 made into the pericardium using a device and method disclosed herein. The balloons can be from two individual catheters or part of a bifurcated catheter 604 as shown. A coronary vessel 605 is illustrated in the procedural field 606 created between the balloons. In the illustrated example, the balloons 600 and 601 create a procedural field 606 around coronary vessel 605 by maintaining the pericardium off the epicardial surface 607 and laterally away from the coronary vessel 605.

It is foreseen that the minimally invasive procedures disclosed herein for accessing the pericardial space can provide a new and advantageous approach for many cardiac procedures including, for example, coronary artery bypass surgery, placement of a vascular graft brachytherapy, etc.

From the foregoing detailed description of the present invention, it has been shown how the objects of the invention can be obtained in a preferred manner. However, modifications and equivalents of the disclosed concepts such as those that would occur to one of ordinary skill in the art, are intended to be included within the scope of the present invention.

We claim:

1. A method for performing a minimally invasive procedure to a patient's heart through a pericardial space to treat a cardiac rhythm disorder, the method comprising a step of:
    (a) forming a minimally invasive incision in the patient's thorax;
    (b) lifting a portion of pericardium away from the patient's heart;
    (c) penetrating through the portion of pericardium into the pericardial space;
    (d) passing an electrophysiology catheter into the pericardial space;
    (e) mapping electrical conductivity of the heart with the electrophysiology catheter to locate a source of an arrhythmia.

2. The method according to claim 1 wherein the step of mapping includes mapping an epicardial surface of the patient's heart.

3. The method according to claim 2 wherein the step of mapping includes mapping an endocardial surface of the patient's heart.

4. The method according to claim 1 wherein the step of lifting includes lifting the portion of pericardium away from the heart with suction.

5. The method according to claim 4 wherein the step of lifting the portion of pericardium away from the patient's heart is performed with a device comprising:
    an outer tubular body having:
        (i) a distal end; and
        (ii) a lumen surrounded by a sidewall through which an applied vacuum can pass; and
    a penetrating body axially mobile within the outer tubular body and having
        a piercing tip suitable for penetrating the portion of pericardium.

6. The method according to claim 5 wherein the distal end of the device is closed and the sidewall has an opening in fluid communication with the lumen near the distal end of the outer tubular body.

7. The method according to claim 1 wherein the step of lifting the portion of pericardium away from the patient's heart is performed by mechanical grasping.

8. The method according to claim 7 wherein the mechanical grasping device comprises:
    (a) at least two grasping surfaces; and
    (b) a piercing body that passes between the at least two grasping surfaces.

9. The method according to claim 1 further comprising treating a cardiac arrhythmia detected by electrophysiological mapping including steps of:
    (e) passing an ablation catheter into the pericardial space at an epicardial surface of the heart to an arrhythmia-causing region; and
    (f) activating the ablation catheter to destroy the arrhythmia-causing region at the epicardial surface of the heart.

10. The method according to claim 9 wherein the ablation catheter uses radio frequency energy to destroy the arrhythmia-causing region.

11. The method according claim 9 wherein the ablation catheter uses laser energy to destroy the arrhythmia-causing region.

12. The method according to claim 9 wherein the ablation catheter uses microwave energy to destroy the arrhythmia-causing region.

13. The method according to claim 9 wherein the ablation catheter uses thermal energy to destroy the arrhythmia-causing region.

14. The method according to claim 13 wherein the thermal energy is freezing.

15. The method according to claim 9 wherein the portion of pericardium is lifted away from the heart with suction.

16. The method according to claim 15 wherein the portion of pericardium lifted away from the heart is performed with a device comprising:
    (a) an outer body having:
        i. a distal end; and
        ii. a lumen surrounded by a sidewall through which an applied vacuum can pass; and
    (b) a penetrating body axially mobile within the outer tubular body and having a piercing tip suitable for penetrating the portion of pericardium.

17. The method according to claim 9 wherein the portion of pericardium is lifted away from the heart by mechanical grasping.

18. The method according to claim 17 wherein the portion of pericardium lifted away from the heart is performed with a device comprising:
    (a) at least two grasping surfaces; and
    (b) a piercing body that passes between the at least two grasping surfaces.

19. The method according to claim 9 wherein the ablation catheter and electrophysiology catheter are integrated into a single device.

20. The method according to claim 9 wherein an endocardial surface of the heart is mapped and the epicardial surface is mapped.

* * * * *